(12) United States Patent
Jang

(10) Patent No.: US 6,806,955 B2
(45) Date of Patent: Oct. 19, 2004

(54) METHOD AND APPARATUS FOR MEASURING FIBER PROPERTIES

(75) Inventor: Ho Fan Jang, Vancouver (CA)

(73) Assignee: Pulp and Paper Research Institute of Canada, Pointe Claire (CA)

(*) Notice: Subject to any disclaimer, the term of this patent is extended or adjusted under 35 U.S.C. 154(b) by 298 days.

(21) Appl. No.: 10/015,787

(22) Filed: Dec. 17, 2001

(65) Prior Publication Data

US 2002/0117274 A1 Aug. 29, 2002

(30) Foreign Application Priority Data

Dec. 21, 2000 (CA) .............................................. 2329294

(51) Int. Cl.$^7$ ................................................. G01J 3/30
(52) U.S. Cl. .................. 356/318; 250/458.1; 250/461.1
(58) Field of Search ................................ 356/318, 317, 356/332, 634, 635, 419, 416, 417; 162/49, 50, 198, 263; 250/458.1, 459.1, 461.1

(56) References Cited

U.S. PATENT DOCUMENTS

| | | | |
|---|---|---|---|
| 4,837,446 A | | 6/1989 | Renard et al. |
| 5,220,172 A | * | 6/1993 | Berthold et al. ......... 250/461.1 |
| 5,293,219 A | | 3/1994 | Ayer |
| 5,311,290 A | | 5/1994 | Olson et al. |
| 5,486,915 A | * | 1/1996 | Jeffers et al. ............... 356/318 |
| 5,530,551 A | | 6/1996 | Cantrall et al. |
| 6,202,493 B1 | * | 3/2001 | Cantrall et al. ............... 73/800 |

OTHER PUBLICATIONS

Seth, R.S. "Fibre Quality Factors in Papermaking–II. The Importance of Fibre Coarseness", in MRS Symposium Proceedings, Materials Research Society, Pittsburgh, P.A., vol. 197, pp. 143–161 (1990).

Paavilainen, L. "Importance of Cross–Dimensional Fibre Properties and Coarseness for the Characterization of Softwood Sulphate Ppulp", Paperi ja Puu 75(5): 343 (1993).

Jang, H. F., Robertson, A.G., and Seth, R.S., "Transverse Ddimensions of Wood Ppulp Fibres by Confocal Laser Scanning Microscopy and Image Analysis", J. Mater. Sci. 27: pp. 6391–6400 (1992).

Seth, R.S., Jang, H.F., Chan, B.K., and Wu, C.B., "Transverse dimensions of wood pulp fibres and their implication for end use", in The Fundamentals of Papermaking Materials; Transactions of the Eleventh Fundamental Research Symposium held at Cambridge: Sep. 1997, edited by C.F. Baker, PIRA International, Leatherhead, UK, pp. 473–503 (1997).

(List continued on next page.)

Primary Examiner—Frank G. Font
Assistant Examiner—Layla Lauchman
(74) Attorney, Agent, or Firm—Ogilvy Renault

(57) ABSTRACT

The invention relates to a fluorescence microscopy technique for measuring physical and chemical properties of individual fiber-like particles. Fluorescence intensity per unit length is shown to be proportional to the fiber coarseness. In addition, other fiber properties such as fiber length, width and wall thickness can be obtained from fluorescence images, and lignin content from fluorescence spectra. The present invention will provide a process for determining the uniformity of pulp samples in terms of the physical and chemical properties of the individual fiber-like particles, particularly wood pulp fibers.

11 Claims, 23 Drawing Sheets

OTHER PUBLICATIONS

Boyer, B., and Rudie, A,. "Measurement of delignification diversity within kraft pulping processes", in TAPPI Proceedings, Pulp Conference, pp. 765–770 (1995).

Liu, Y., Gustafson, R., Callis, J., and McKean, W., "A novel method to measure fibre kappa number", TAPPI J. 82(9), pp. 107–111 (1999). Liu, Y., Gustafson, R., Calis, J., and McKean, W., "Microspectroscopic analysis and kappa determination of single pulp fibres stained with acridine orange", J. Pulp Paper Sci. 25(10), pp. 351–355 (1999).

Olmstead, J. A. and Gray, D. G., "Fluorescence spectroscopy of cellulose, lignin and mechanical pulps: a review", J. Pulp and Paper Science 23(12), pp. 571–581 (1997).

Carlsson, J., Malmqvist, L., Nilsson, C.M. and Persson, W., , "Application of optical fluorescence spectroscopy to paper production", Preprints, TAPPI Int. Paper Physics Conference, San Diego, pp. 429–436 (1999).

Sprent, P., "Applied Nonparametric Statistical Methods", Second edition, Chapman & Hall, New York, 1993.

G18—Kappa Number of Pulp, Standard Methods of the Technical Section of the CPPA, Montreal; "T236—Kappa Number of Pulp", TAPPI Standard Methods, Tappi Press, Altanta.

* cited by examiner

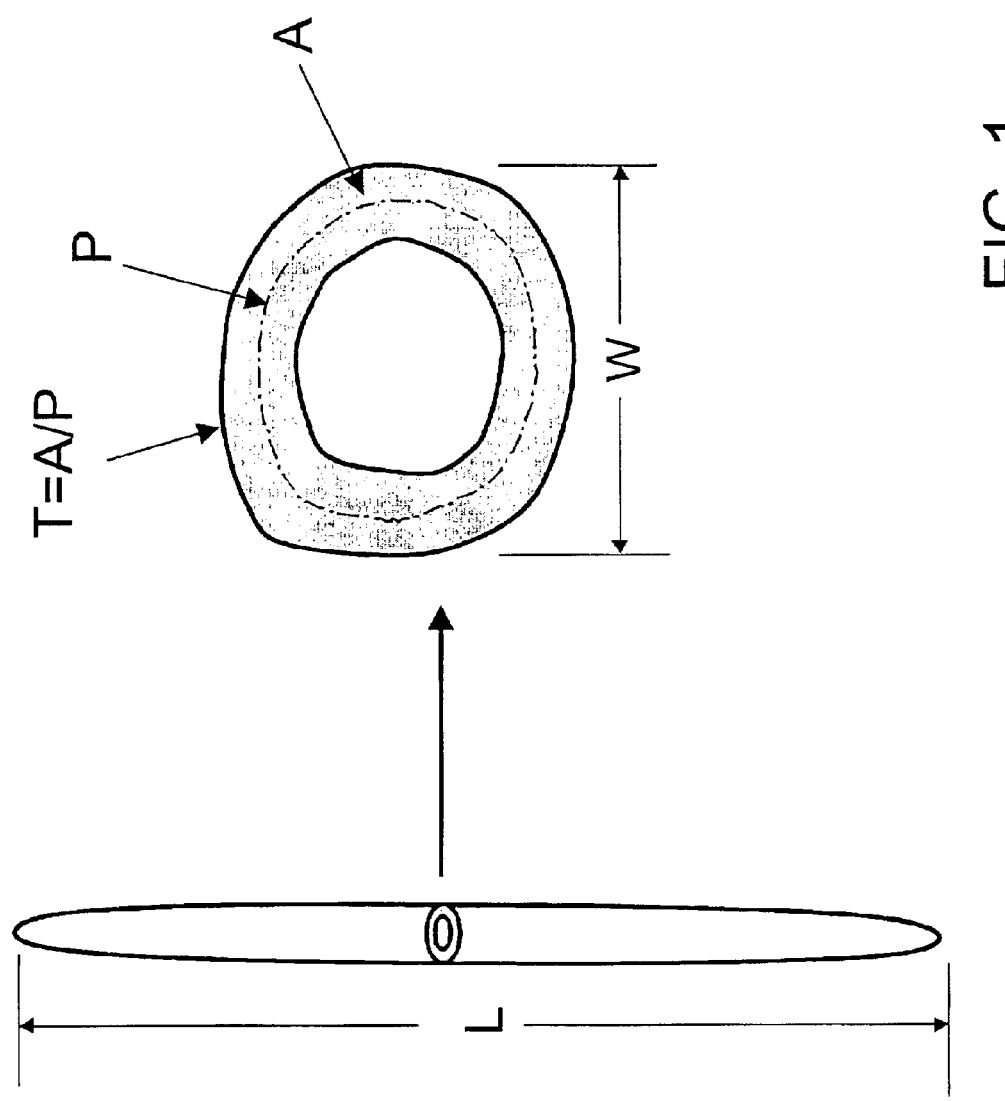

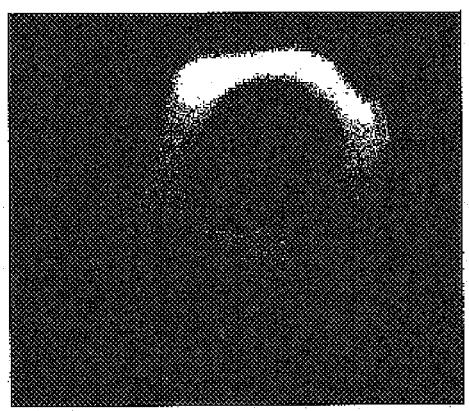
FIG. 2a
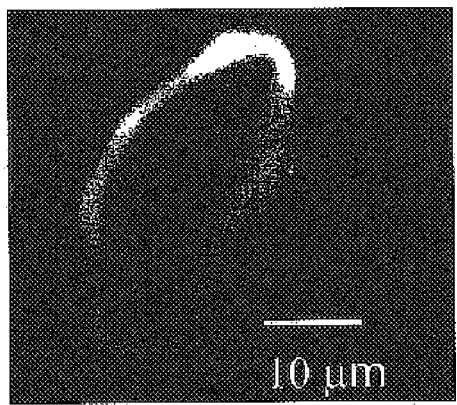
FIG. 2b
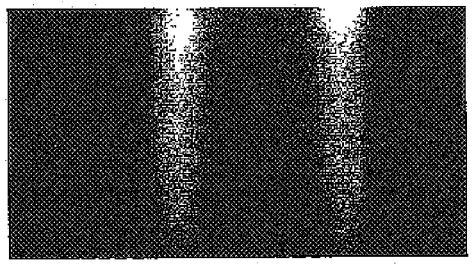
FIG. 2a1
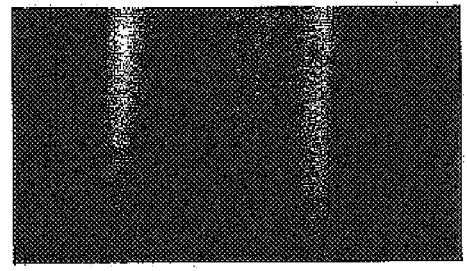
FIG. 2b1

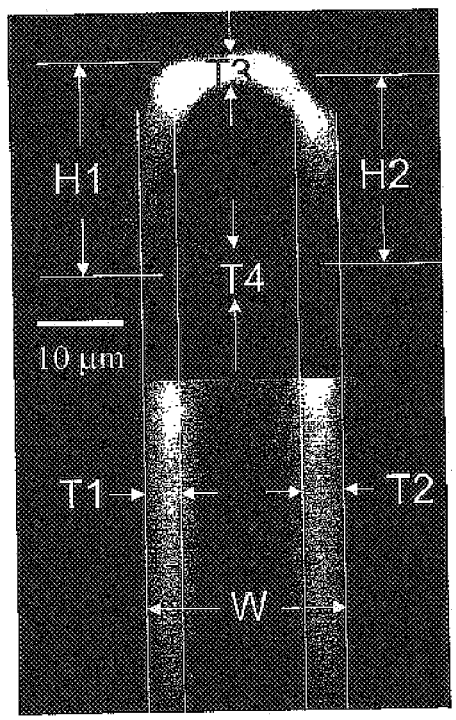
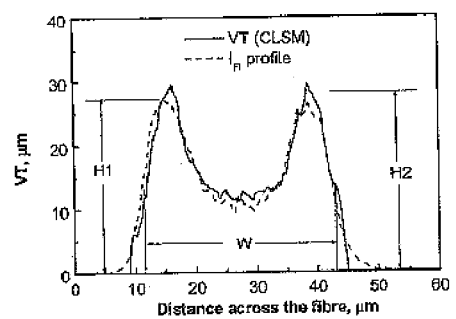
FIG. 6b
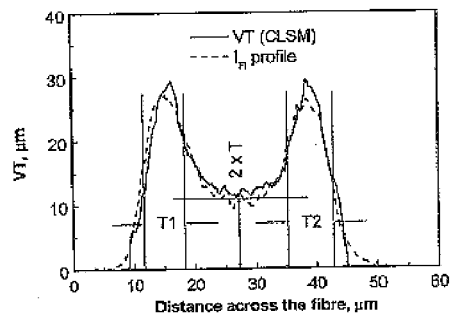
FIG. 6c
FIG. 6a

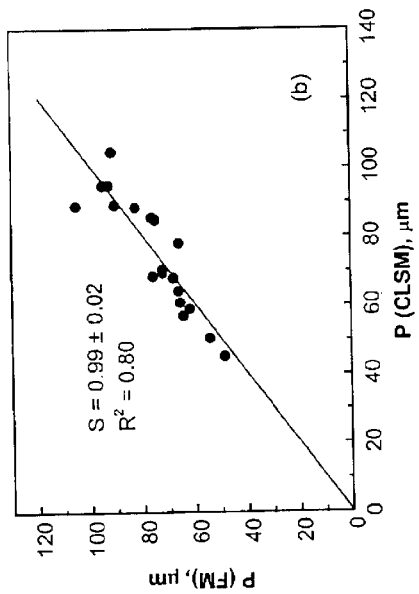
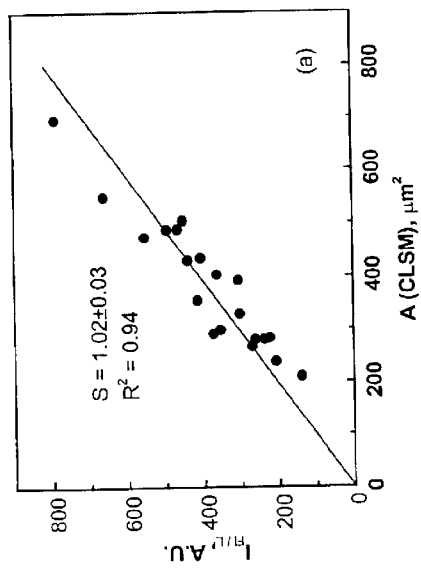
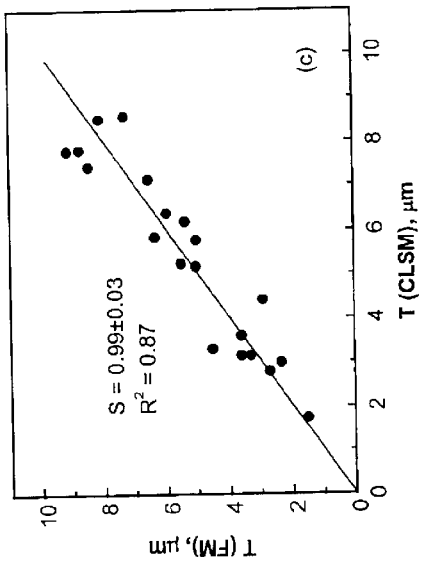
FIG. 8a
FIG. 8b
FIG. 8c

METHOD AND APPARATUS FOR MEASURING FIBER PROPERTIES

FIELD OF INVENTION

The present invention relates, in general, to the pulp and paper industry, and in particular, to a new and useful apparatus and method or technique for rapid and accurate measurements of physical and chemical properties of individual wood pulp fibres such as fibre coarseness, width, wall thickness, and lignin content.

BACKGROUND OF THE INVENTION

To ensure paper quality, it is important to know the physical properties of wood pulp fibres used in papermaking. Important properties include fibre length, and transverse dimensions such as cross-sectional area, width, perimeter, and wall thickness as shown in FIG. 1 [1,2]. While the major effect of fibre length is on the sheet strength, fibre transverse dimensions affect all paper properties structural, strength, and optical. Unfortunately, many important fibre transverse dimensions have been difficult to measure. Moreover, all fibre properties are distributed in nature. The information on the distributions of fibre properties is considered more important than their mean values in controlling pulp quality as it provides the extent of heterogeneity in a pulp, and allows us to identify the amount of fibres with undesirable properties.

Fibre coarseness, defined as mass per unit length and related to the fibre cross-sectional area by the density of fibre wall materials, is an important fibre property [1,2]. Optical instruments, such as the Kajaani fibre length analyser (Kajaani Electronics Ltd, Finland), the Fibre Quality Analyser (Optest, Canada)[P1], and fibre length analyser (Andritz Sprout-Bauer, Inc., US) [P2] were developed for the rapid determination of fibre-length distribution. If the total mass of pulp fibres being measured is known, these instruments will calculate population-average fibre coarseness. This technique can neither provide the information on fibre coarseness distribution, nor be implemented for an on-line measurement of coarseness. A rapid and accurate method for measuring the coarseness of individual wood pulp fibres is not yet available because of their extremely small weight and irregular shape.

Fibre wall thickness is another important fibre property. Two fibres of similar coarseness can have quite different wall thickness if their perimeters are different. Recently, a new instrument, Kajaani FibreLab fibre analyzer, provides measurements for fibre width and cell wall thickness of fibres flowing through a capillary tube [P5]. The principle of this instrument is based on microscopic imaging. This measurement technique is quite adequate for fibre width because its dimension is in the range of tens of microns.

However, this direct imaging technique faces many difficulties for accurate fibre wall thickness measurements. First, an accurate measurement for fibre wall thickness, which is in the range of a few microns, requires high resolution, and therefore, high precision optics and precise focusing. Precise focusing is difficult to accomplish for a flowing fibre. Second, the measurement is based on the projected two-dimensional image of a fibre. The interpretation of image can be complex and difficult. Third, this wall thickness measurement, at best, is obtained only from two sides of the fibre, but not around the whole fibre. Therefore, the measurement depends on the orientation of the fibre, as the wall thickness varies around the fibre. And finally, the direct imaging method can only measure the apparent fibre wall thickness that depends on the degree of fibre wall swelling and delamination, or external fibrillation, but not the true fibre wall thickness. Thus, a rapid and accurate technique for measuring the wall thickness of individual fibres is still lacking.

Recently, a nondestructive procedure has been developed for obtaining cross-sectional images of wood pulp fibres using the optical sectioning ability of confocal laser scanning microscopy (CLSM) [3]. When combined with image analysis, this technique is capable of accurately measuring individual fibre transverse dimensions, such as wall thickness and cross-sectional, hence, fibre coarseness [4]. Although this technique provides much valuable information on fibre quality, and is a good research tool, it is too slow for most practical purposes. A new rapid technique with similar or comparable accuracy as in the CLSM technique for measuring individual fibre transverse dimensions is needed.

In a chemical pulp manufacturing process, the production of wood pulp fibres and/or paper products from wood chips is by removing, either partially or entirely, lignin from the wood. Lignin content is an important quality parameter and property for chemical pulp fibres. The amount of lignin left in a pulp after chemical pulping process is measured in terms of Kappa number. There are a few commercial Kappa Number Analyzers available for measuring the Kappa number in a pulp. However, the importance of uniformity to product quality arises not only from the physical properties of fibres, but also from their chemical properties. Unfortunately, few data are available on lignin content variability within and between individual fibres. Methods to determine the kappa number of individual pulp fibres include use of a density gradient column and Fourier transform infrared (FTIR) microscopic analysis [5], and an intensity measurement of primary fluorescence [P4]. Recently, Liu et al. described a method based on fluorescence microphotometry of fluorescent stained fibres [6]. However, these methods are either too slow or not reliable. There is as yet no rapid and reliable technique or apparatus for measuring the lignin content/Kappa number of individual fibres.

It is known that wood, pulp and paper samples exhibit inherent fluorescence. This fluorescence is the sum of the fluorescence from cellulose, hemicellulose, lignin and the lignin artefacts generated during the pulping process [7]. The fluorescence spectra of mechanical and chemical pulp sheets have been investigated in a number of studies. In general, these studies found similar broadband emission spectra for all pulp sheet samples at a given excitation wavelength. For example, the fluorescence emission spectra obtained using 350 nm excitation light have broad, structureless bands between 375 and 600 nm, and have maxima around 450 nm.

Fluorescence from wood fibres is a very complex process. It is known that fluorescence from paper or pulp is a highly non-linear function of sheet basis weight or grammage and the excitation wavelength. It also shows an unpredictable dependence on lignin content. For example, increasing lignin content can lead to a decrease in fluorescence because of re-absorption mechanism [8]. Thus, it is uncertain whether fluorescence intensity can be used for quantifying physical and chemical properties of wood pulp fibres. Recently, techniques based on optical fluorescence spectroscopy have been used in determining the chemical composition, for example, the local abundance of lignin in paper [8]. Jeffers et al. described a method for on-line measurement of lignin in wood pulp by color shift of fluorescence [P3]. However, these techniques suffer from the problems normally associated with the fluorescence from pulp and paper. For instance, decreasing lignin content is shown to produce an increase in fluorescence intensity. The fluorescence spectra are expected to be affected by the above-mentioned problems.

The mismatch of refractive indexes in fibres and water create optical discontinuities in the fibre wall and water interfaces. Methods based on optical methods for measuring transverse dimension measurements on fibres suspended in water face issues such as interferences from light scattering. Moreover, optical measurements depend on the complex relationship between optical properties, light scattering, and orientations of the fibres being evaluated.

Therefore, there is still a need for a rapid and accurate technique for measuring physical and chemical properties of individual fibres.

SUMMARY OF THE INVENTION

It is an object of this invention to provide a method of determining physical and chemical properties of particles, especially wood pulp fibres.

It is another object of this invention to provide an apparatus for determining physical and chemical properties of particles, especially wood pulp fibres.

In one aspect of the invention there is provided a method of determining a physical or chemical parameter of wood pulp comprising: a) applying excitation light at at least one predetermined wavelength to wood pulp, to produce fluorescence emission light from individual fibre particles of the wood pulp, b) detecting fluorescence intensities of said fluorescence emission light, for each said predetermined wavelength, and c) determining a physical or chemical parameter of individual fibre particles of the wood pulp from said fluorescence intensities.

In another aspect of the invention there is provided an apparatus for determining a physical or chemical parameter of wood pulp comprising: i) means to apply excitation light at at least one predetermined wavelength to wood pulp, to produce fluorescence emission light from individual fibre particles of the wood pulp, ii) detection means for detecting fluorescence intensities of the fluorescence emission light for each predetermined wavelength, and iii) means for determining a physical or chemical parameter of individual fibre particles of the wood pulp from the fluorescence intensities.

The invention relies mainly on fluorescence properties of fibre-like particles to provide a method, and apparatus or measurement instruments implementing the method to measure physical and chemical properties of individual fibre-like particles, in particular wood pulp fibres, simultaneously if needed.

BRIEF DESCRIPTION OF THE DRAWINGS

FIG. 1 shows a fibre with length L, and its cross-sectional area A, width W, center-line perimeter P, and wall thickness T. The mean fibre wall thickness of a fibre cross section is A/P;

FIGS. 2(a), (a1), (b) and (b1) show two confocal cross-sectional images of fibres immersed in water and their respective fluorescence images;

FIGS. 6(a), (b) and (c) show that various transverse dimensions of fibres, such as wall thickness T1 and T2, and T3 and T4, vertical fibre wall thickness H1 and H2, and fibre width W can be generated from their fibre fluorescence images;

FIGS. 8(a), (b) and (c) are graphs of transverse dimensions obtained from fluorescence technique versus those from confocal microscopy for unbleached softwood chemical pulp fibres;

DETAILED DESCRIPTION OF THE INVENTION

The present invention uses fluorescence intensities of undyed or dyed fibres in a technique for measuring individual fibre transverse dimensions and lignin content accurately and rapidly. The present invention for measuring fibre transverse dimensions is validated by the established CLSM technique. The new measurement on the lignin content of fibres is compared with the Kappa number of the pulp, obtained by standard methods.

Fibre Transverse Properties

Experimental results show that if a sample such as fibre-like particle is excited with a wavelength in a weak absorption region, which can range from ultraviolet to visible wavelength, the fluorescence intensity $I_{FL}$ is found to be proportional to the sample thickness d:

$$I_{FL} \propto I_o d,$$

where $I_o$ is the intensity of excitation light. Most wood, pulp and paper samples are known to have absorption peak near 280 nm. The excitation wavelength is chosen such that absorption in the sample, such as in an individual fibre, is weak, and sufficient fluorescence intensity can be generated for suitable detection. For example, the results shown in here were generated with the excitation in the wavelength region ranged from 360 nm (ultraviolet) to 500 nm (visible). In general the excitation may be in the wavelength region 5 nm to 700 nm, preferably 250 nm to 600 nm.

Typical confocal cross-sectional images [3] and fluorescence images of wood pulp fibres immersed in water were generated simultaneously as shown in FIGS. 2a, 2a1, 2b and 2b1. The fibre's gray level in the fluorescence images is proportional to the fluorescence intensity. The vertical wall thickness and fluorescence intensity profiles generated from the images in FIGS. 2a, 2a1, 2b and 2b1 are shown to be consistent as presented in FIGS. 3a and 3b.

Figure 3B:
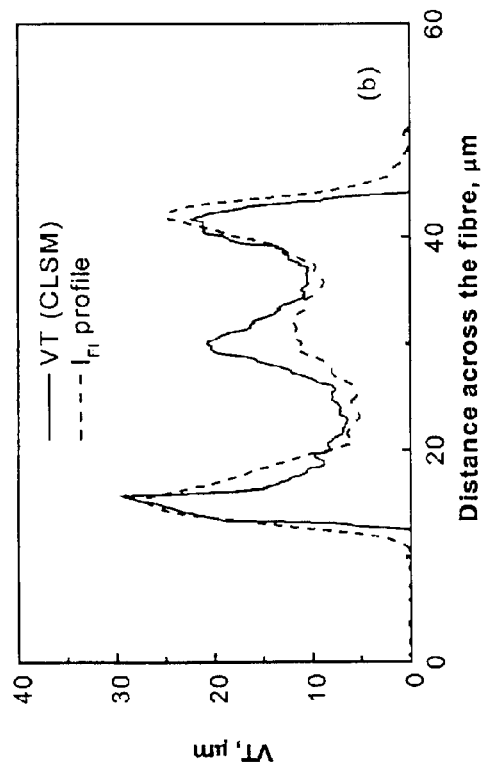
FIGS. 3(a) and (b) show vertical wall thickness VT ($\mu$m) and fluorescence intensity profiles along the distance across the fiber ($\mu$m) for the two fibres in FIGS. 2a, 2a1 and 2b1, 2b2. The fluorescence intensity profiles across the fibres were obtained at the same locations where the confocal cross-sectional images were generated. Similarity of these profiles confirms that light scattering does not significantly affect the use of fluorescence intensity to quantify fibre wall thickness.
Figure 3A:
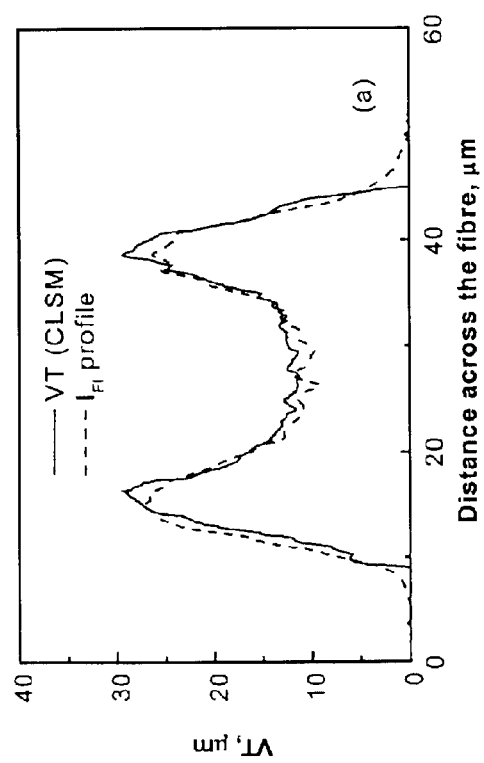

Analyzing the fluorescence intensity profiles can generate many important fibre transverse dimensions. For example, fibre cross-sectional area is proportional to the area under the fluorescence intensity profile as shown in FIGS. 3a and 3b. Also, fluorescence intensity is proportional to the mass of material. Fibre coarseness is defined as mass per unit fibre length, and therefore corresponds to the total fluorescence intensity divided by the length of fibre being excited.

Figure 4:
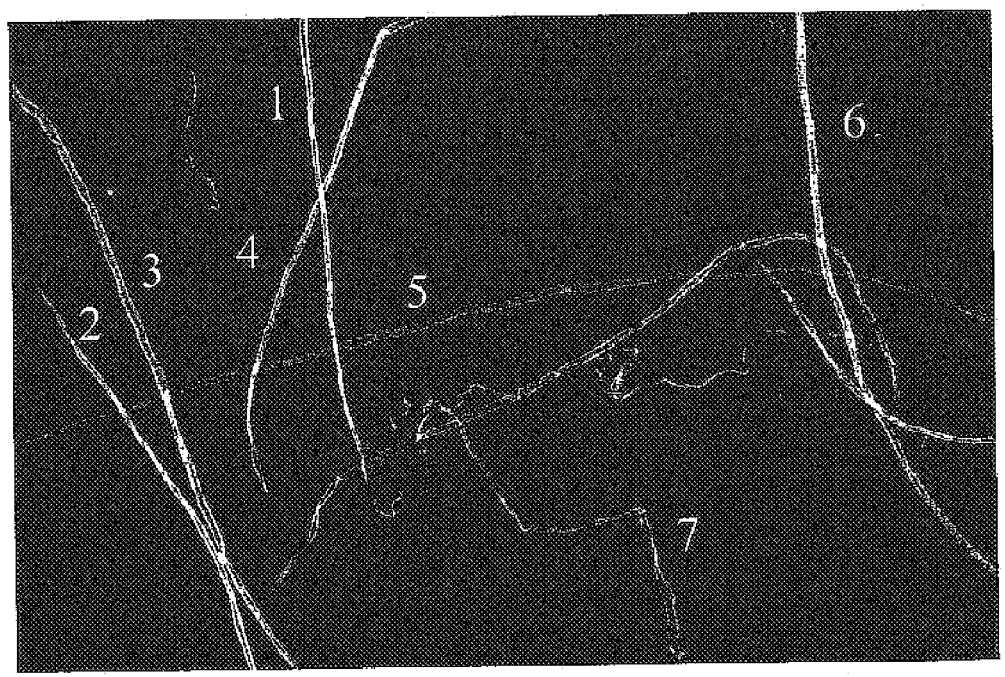
FIG. 4 is a typical fluorescence image of unbleached softwood kraft pulp wood fibres. The fluorescence intensities per unit length, with background removed, and their cross-sectional areas by confocal microscopy for several fibres at the locations indicated were determined.
Figure 5:
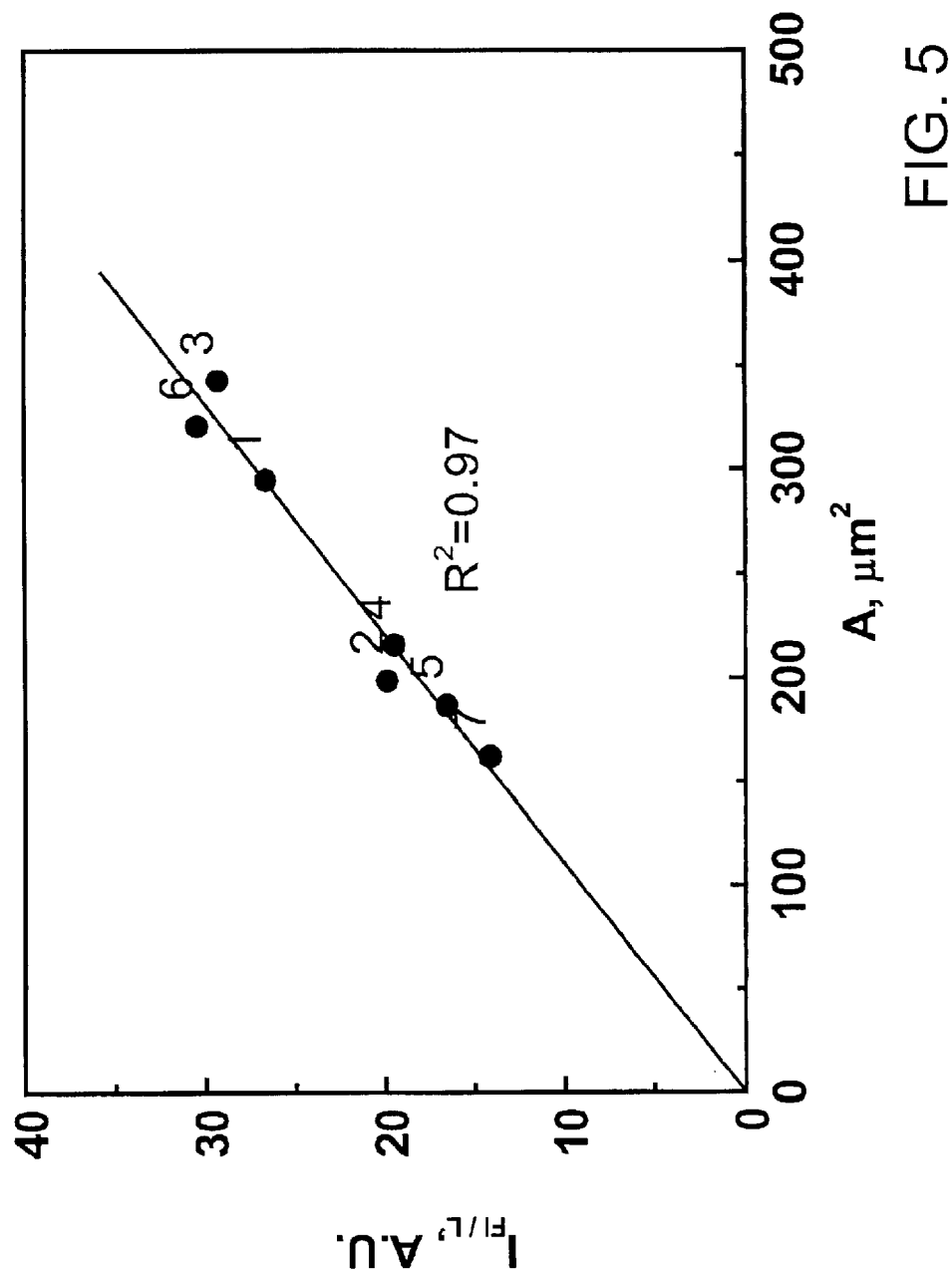
FIG. 5 shows a strong correlation between fluorescence intensity per unit length $I_{FI/L}$ and fibre cross-sectional area A for the measurements shown in FIG. 4. The units for $I_{FI/L}$ and A are arbitrary unit AU and $\mu m^2$ respectively.

FIG. 4 shows a typical fluorescence image of wood pulp fibres. The fluorescence intensities per unit length at the locations indicated were determined. The fibre cross-sectional area generated for these sections of fibres was also determined simultaneously using confocal microscopy technique. FIG. 5 shows the coefficient of determination ($R^2$) to be 0.97. This confirms a strong correlation between fibre cross-sectional area and fluorescence intensity per unit length.

The above results demonstrate that the problems, normally associated with fluorescence from paper or pulp, are not found in the fluorescence in here when fluorescence is obtained on an individual fibre excited in a weak absorption region. In addition, other expected problems, such as light scattering in the fibre-wall interfaces, which is critical in other optical methods, are found to be insignificant for these measurements.

The projected fibre width can be determined from the boundary of the fluorescence image as illustrated in FIGS. 6a, 6b and 6c. The widths of the peaks on both sides, T1 and T2, can be used to estimate the fibre wall thickness, particularly for uncollapsed fibres.

Figure 7:
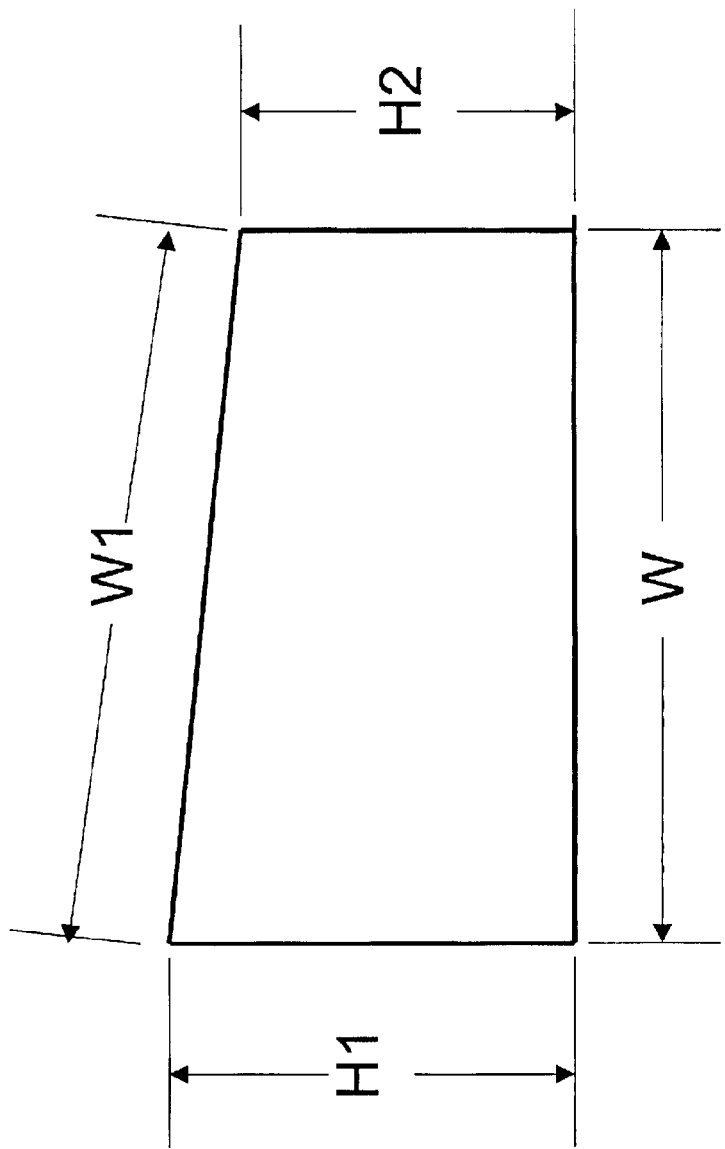
FIG. 7 shows an estimation of outer fibre perimeter OFP from parameters obtained from fluorescence image.

If the calibration factor between fluorescence intensity and fibre cross-sectional area is known, the pixel intensity can be related to the thickness of fibre wall material at that pixel location. For instance, the fluorescence intensity in the middle of the fibre can be used for estimating the double wall thickness. The peaks in the fluorescence image can be related to vertical fibre wall thickness, H1 and H2. The outer fibre perimeter (OFP) can be estimated from adding up the fibre width W, H1, H2, and the calculated W1 together as shown in FIG. 7.

Figure 9A:
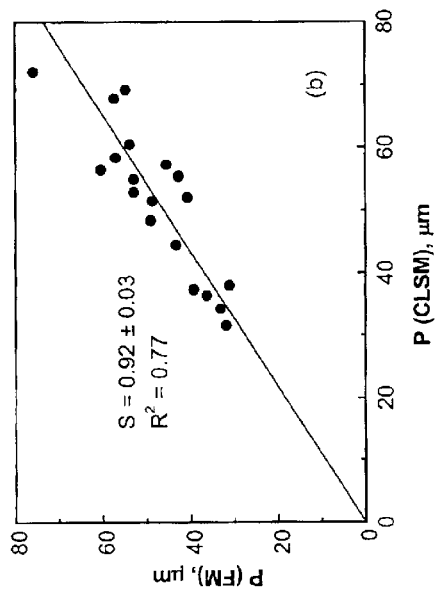
FIGS. 9(a), (b) and (c) are graphs of transverse dimensions obtained from fluorescence technique versus those from confocal microscopy for unbleached hardwood chemical pulp fibres.
Figure 9B:
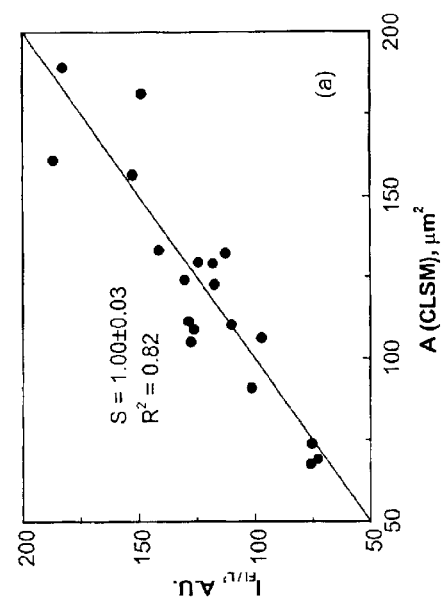
Figure 9C:
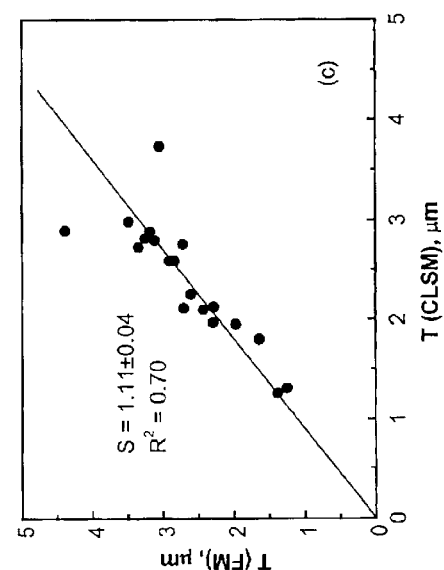

With known fibre cross-sectional area and OFP, mean wall thickness and centre-line perimeter of a fibre can be calculated with a few iterations by a computer. This method of finding fibre wall thickness is far better, easier and more accurate than the direct imaging technique. As shown in FIGS. 8a, 8b and 8c, fibre transverse dimensions, such as wall cross-sectional area A, centre-line perimeter P, and wall thickness T obtained from the fluorescence images are in good agreement with those obtained from confocal microscopy technique for softwood pulp fibres immersed in water. FIGS. 9a, 9b and 9c show this technique works for hardwood pulp fibres as well. In FIGS. 8a, 8b, 8c; and 9a, 9b and 9c, $I_{FI/L}$ indicates fluorescence intensity per unit length in arbitrary units and FM refers to the measurements obtained by fluorescence microscopy technique in $\mu$m; and S identifies slope.

Figure 10:
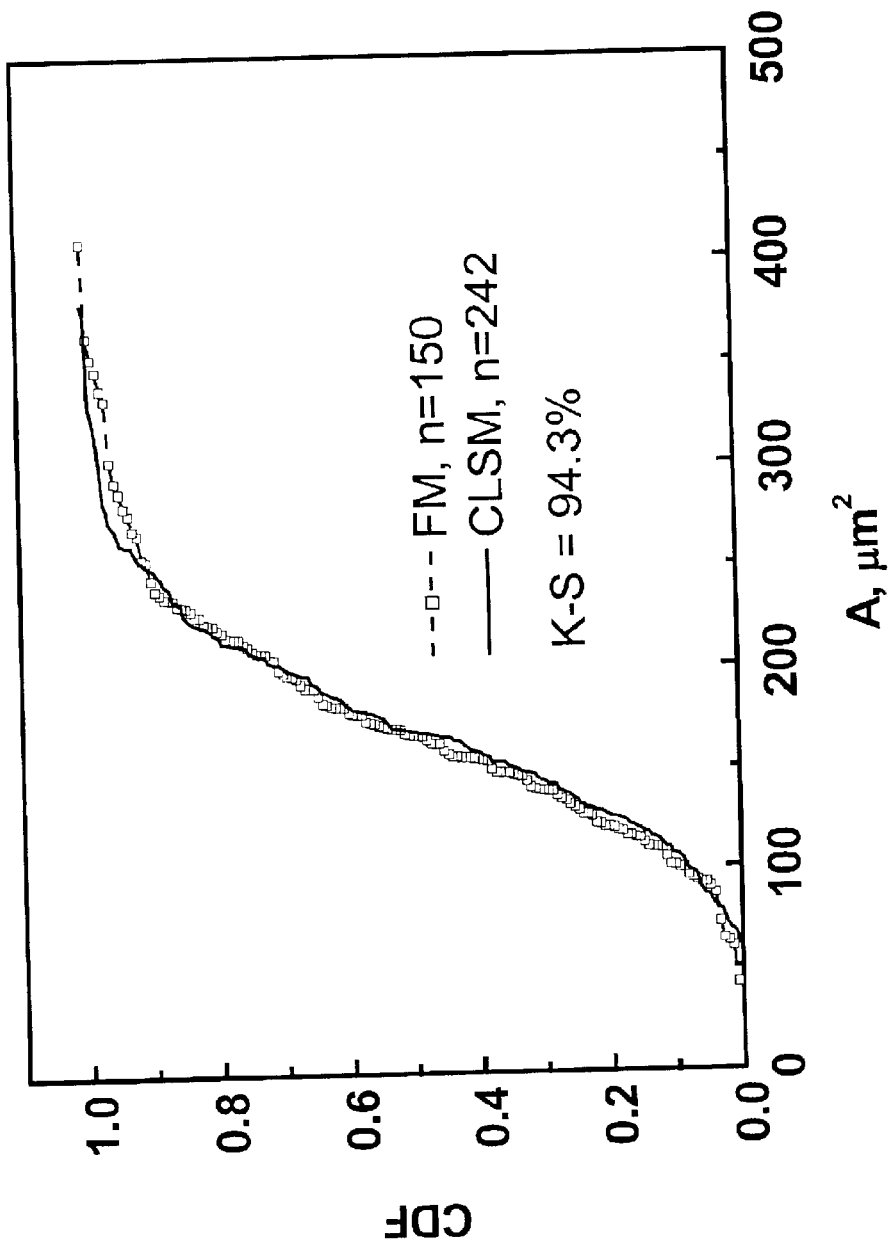
FIG. 10 shows a graph of fibre fluorescence intensity per unit length and cross-sectional area cumulative distribution functions CDF of an unbleached softwood chemical pulp.

A single detector can be used for very rapid measurement of fluorescence intensity. The fluorescence intensity from either a fibre of a known length or a portion of fibre being irradiated will provide the information on fibre coarseness as discussed with reference to FIGS. 22 and 23. FIG. 10 shows the empirical cumulative distribution function CDF of the fluorescence intensity per unit length $I_{FI/L}$ of fibres in unbleached softwood chemical pulp fibres generated by a photomultiplier tube detector and that of fibre cross-sectional areas obtained using confocal microscopy technique CLSM. The Kolmogorov-Smirnor (K-S) test shows a high significant level of 94.3% for these two distributions [9]. This simple fluorescence system can be combined with other optical measurement techniques for other fibre properties, such as transmission imaging for fibre width and/or fibre length. Fibre wall thickness can be estimated from the fibre coarseness and width measurements obtained from fluorescence and transmission imaging techniques respectively.

This fluorescence intensity technique quantifies not only fibre coarseness, but also the mass of individual fines and shives, which is very difficult to measure with any other technique. These fine and shive measurements are very useful, particularly for the quality of thermomechanical pulps. This technique also allows us to investigate fibre properties (both physical and chemical) along a fibre as demonstrated in the fluorescence image shown in FIG. 4. Therefore, this new invention can determine the variability not only between but also within individual fibres.

In comparison with other techniques, the fluorescence technique is relatively fast, simple, sensitive, and robust.

The method requires only minimal sample preparation (similar to that for fibre length measurement in a flow-through system). Dyeing is not required except for very low fluorescence samples. Fibre properties can be measured on wood pulp fibres in either wet or dry state. The technique does not require high precision optics or precise focusing, since intensity measurements do not require high resolution. These advantages are particularly important in flow-through systems for measurements such as fibre coarseness and wall thickness. Results show that the fluorescence measurements can be done for all types of fibre with a wide range of excitation wavelengths. Moreover, the technique does not require complex computation to interpret the data. The necessary requirements are a calibration factor for pulps with different fluorescence properties, an efficient system for collecting the fluorescence signal, and a sensitive detector. The calibration factor for a pulp can be easily obtained as follow. If the total mass and length of the pulp fibres are measured, population-average fibre coarseness could be calculated from the mass divided by the length. The average fibre coarseness could then be used to calibrate the mean fluorescence intensity.

Figure 11:
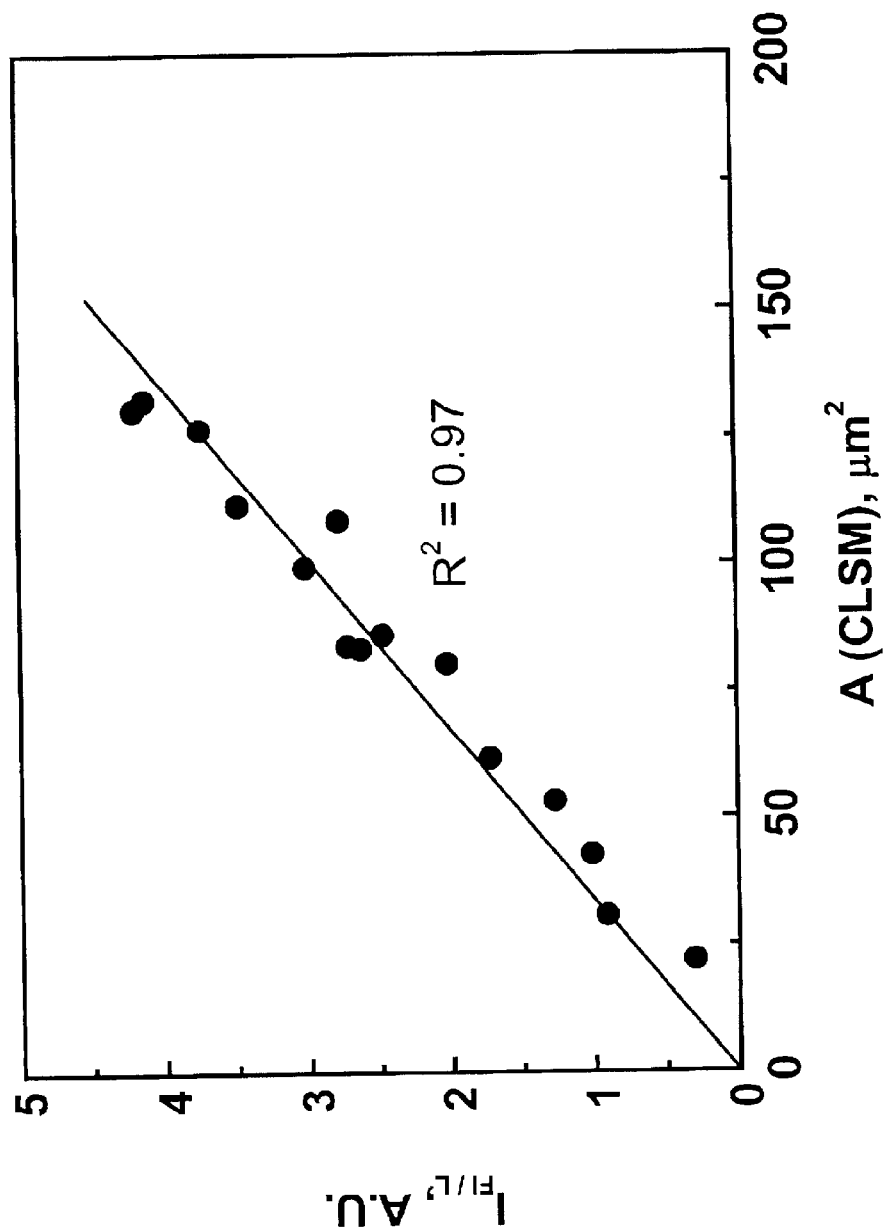
FIG. 11 shows a graph of fluorescence intensity per unit length versus cross-sectional area for hardwood fully bleached chemical pulp fibres. Fibres were lightly dyed with a fluorochrome.
Figure 12:
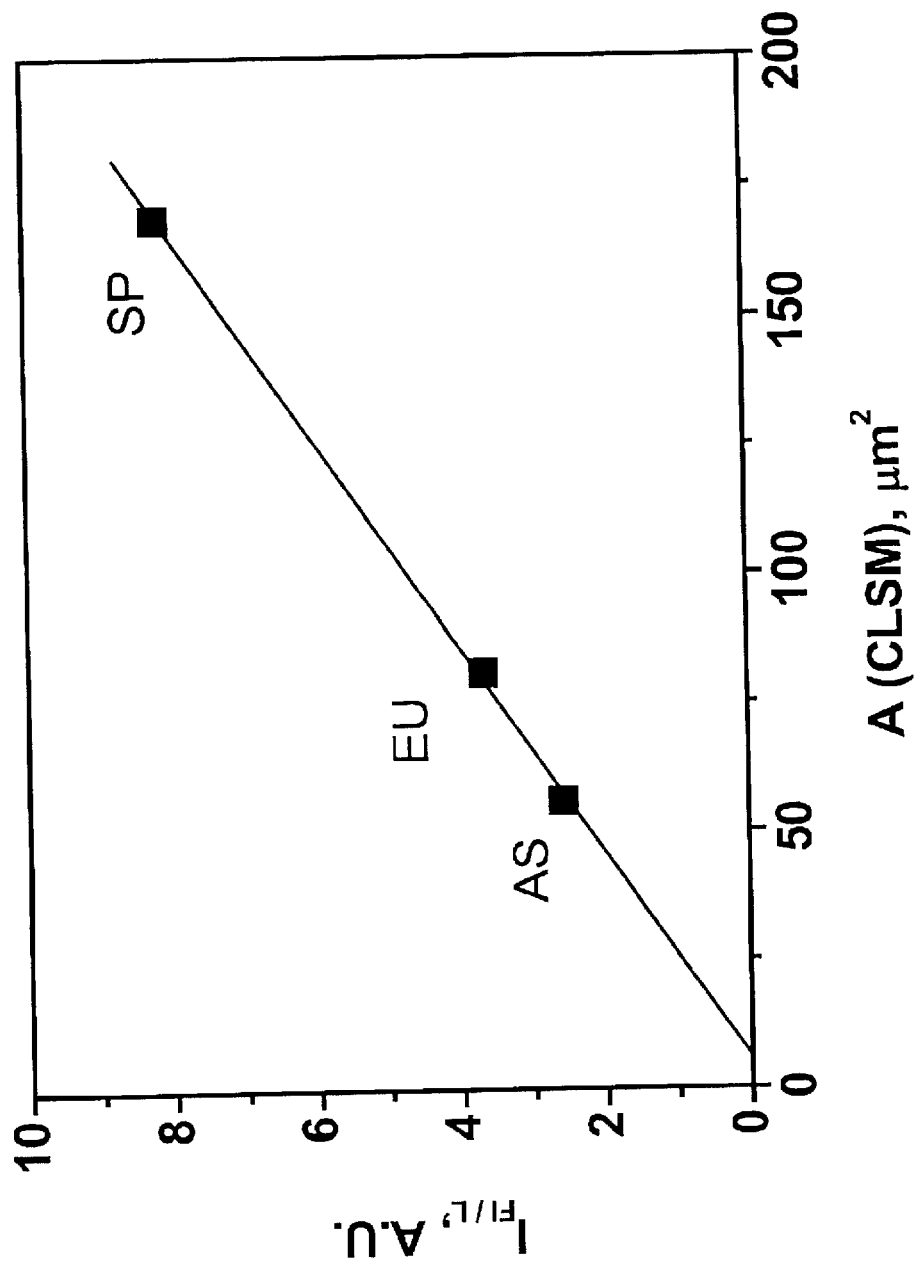
FIG. 12 shows the correlation between fibre fluorescence intensity per unit length and cross-sectional area of three fully bleached pulps.

For some wood pulp fibres such as fully bleached kraft pulp fibres, their auto-fluorescence is very low. The low fluorescence fibres can be lightly dyed with a fluorochrome dye to enhance their fluorescence. FIG. 11 shows a good correlation between the fluorescence intensity per unit length $I_{FI/L}$ and cross-sectional area A for fully bleached hardwood kraft pulp fibres, lightly dyed with a household fabric dye. When the same dyeing conditions are applied to fully bleached kraft pulp fibres of different hardwood and softwood species, the same calibration factor is applied regardless of the species. This is demonstrated in FIG. 12 where the correlation between the means of fibre fluorescence intensity per unit length and cross-sectional area of three different pulps as per aspen, AS, eucalyptus EU and southern pine SP, is excellent.

Figure 13:
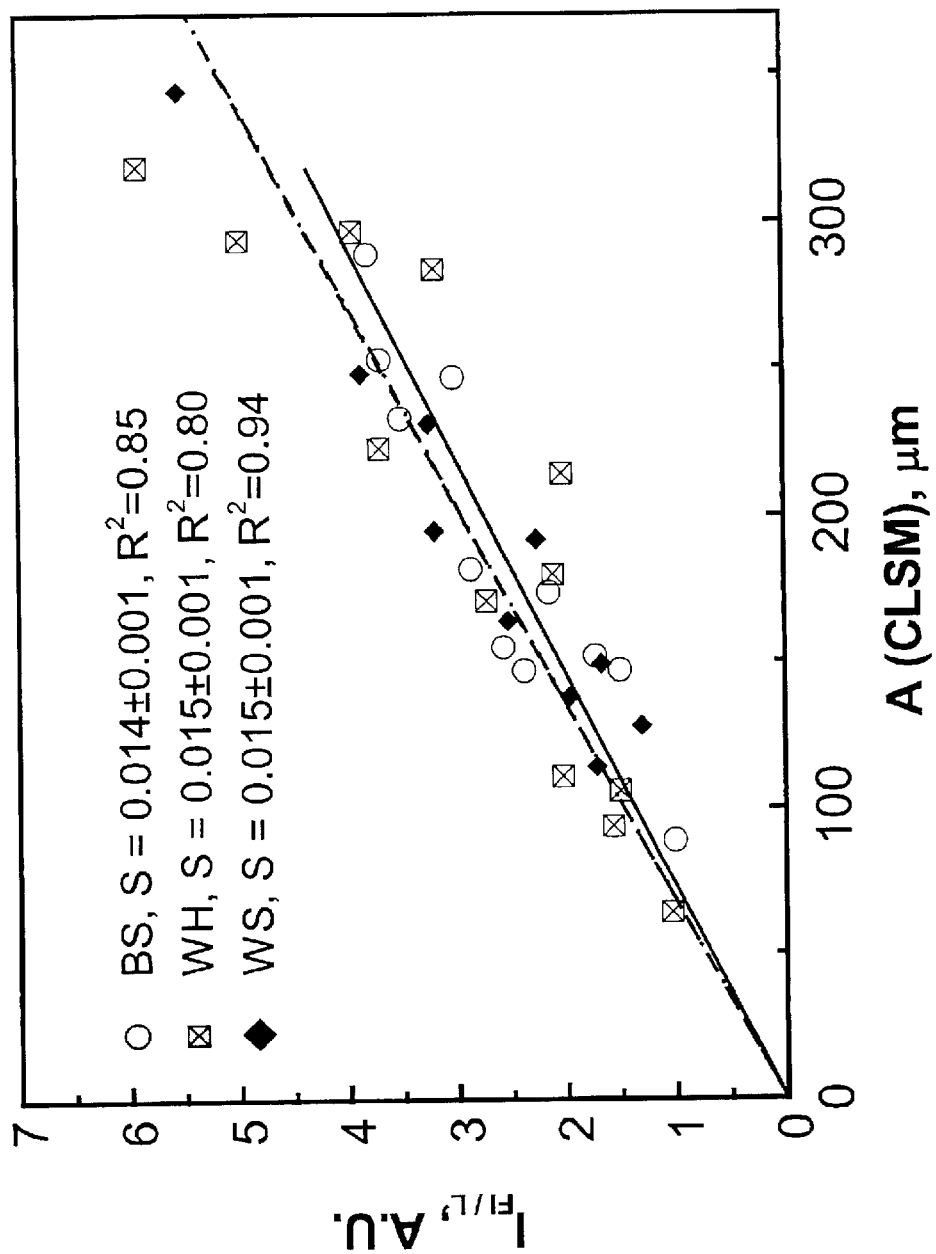
FIG. 13 shows a correlation between fluorescence intensity per unit length and fibre cross-sectional area for thermomechanical pulp fibres of three different species: black spruce (BS), western hemlock (WH), and western spruce (WS)

FIG. 13 shows the fluorescence intensity per unit length $I_{FI/L}$ versus cross-sectional area A for thermomechanical pulp (TMP) fibres of three different species black spruce BS, western hemlock WH and western spruce WS. The best correlation is found when the wavelength of excitation light is in the region from ultraviolet to deep violet. It is also shown that all three species had a similar correlation. This suggests that one calibration factor could be applied to TMP fibres from most species. The units AU for fluorescence intensity per unit length $I_{FI/L}$ are arbitrary units.

Figure 14:
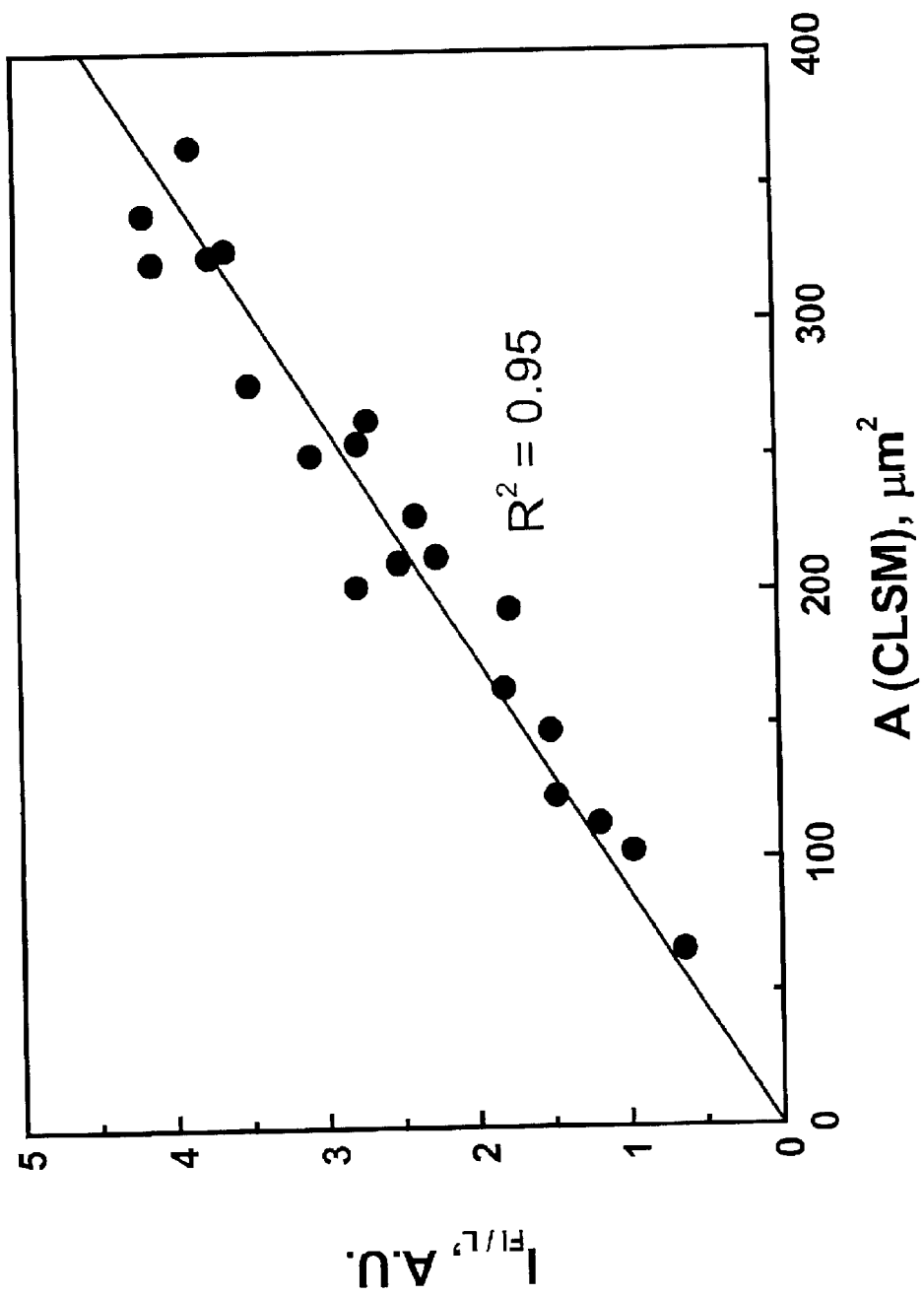
FIG. 14 shows a graph of fluorescence intensity per unit length versus cross-sectional area for fibres of unbleached mixed softwood species chemical pulp.

FIG. 14 shows a good correlation between the fluorescence intensity per unit length $I_{FI/L}$ and cross-sectional area A of unbleached softwood kraft pulp fibres of mixed species cooked at the same time. It is shown that if fibres are cooked to have similar Kappa number, their calibration factors are very similar.

Figure 15:
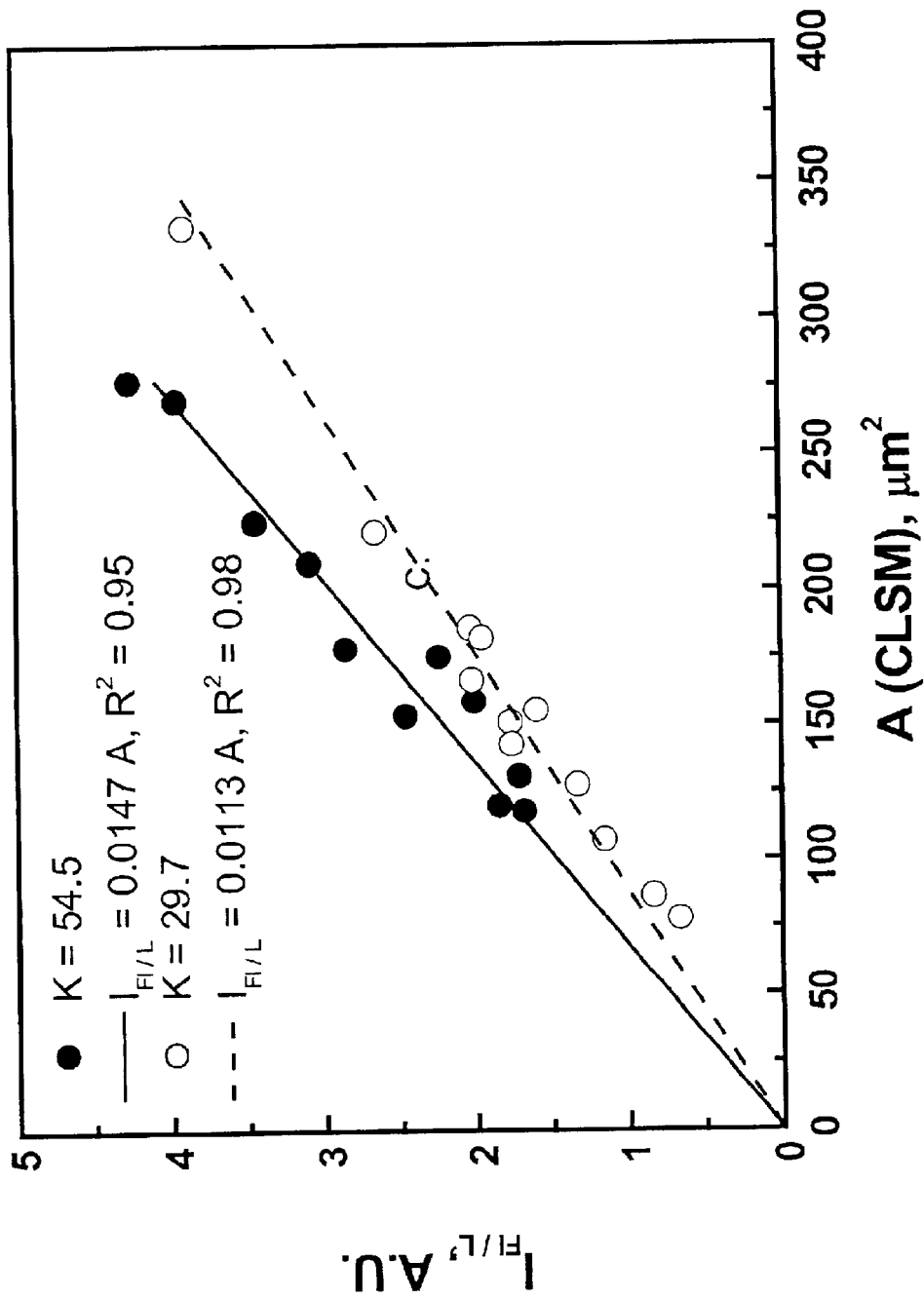
FIG. 15 shows a graph of fluorescence intensity per unit length versus cross-sectional area for fibres of two unbleached softwood chemical pulps with two different Kappa numbers.

The calibration factor depends on the lignin content and its fluorescence property in those fibres. Fibres with different lignin content are expected to have different calibration factors as shown in FIG. 15 for unbleached softwood chemical pulp fibres with two different Kappa numbers. Pulp fibres with higher lignin content, hence, higher Kappa number, have stronger fluorescence intensities per unit length $I_{FI/L}$ at the same cross-sectional areas A. The increased lignin content leading to an increase in fluorescence is in contrast to the normal fluorescence results from pulp and paper, the fluorescence from individual fibres eliminates complicated problems such as re-absorption.

Lignin Content of Individual Fibres

This section will show the technique for determining the lignin content or Kappa number of an individual wood pulp fibre, allowing the characterization of the uniformity of lignin content of a pulp after chemical pulping process. Moreover, this measurement of the lignin content or Kappa number of fibres can be used for modifying the calibration factor used for the above coarseness measurements of fibres with different lignin contents.

The present invention can determine the lignin content or Kappa number of individual fibres from the ratio of the fluorescence intensities obtained with two barrier/long-pass/band-pass filters in or at different regions of wavelengths. This is different from the fluorescence intensity method described by Renard et al [P4] for the lignin measurement of individual fibre. As shown in this invention, the fluorescence intensity per unit length of an individual fibre is strongly related to the fibre coarseness rather than to the lignin content of the fibre. This invention is based on the primary fluorescence of individual fibres, but not on the secondary fluorescence of a fluorescent stained fibre as described in Liu et al[6].

Figure 16:
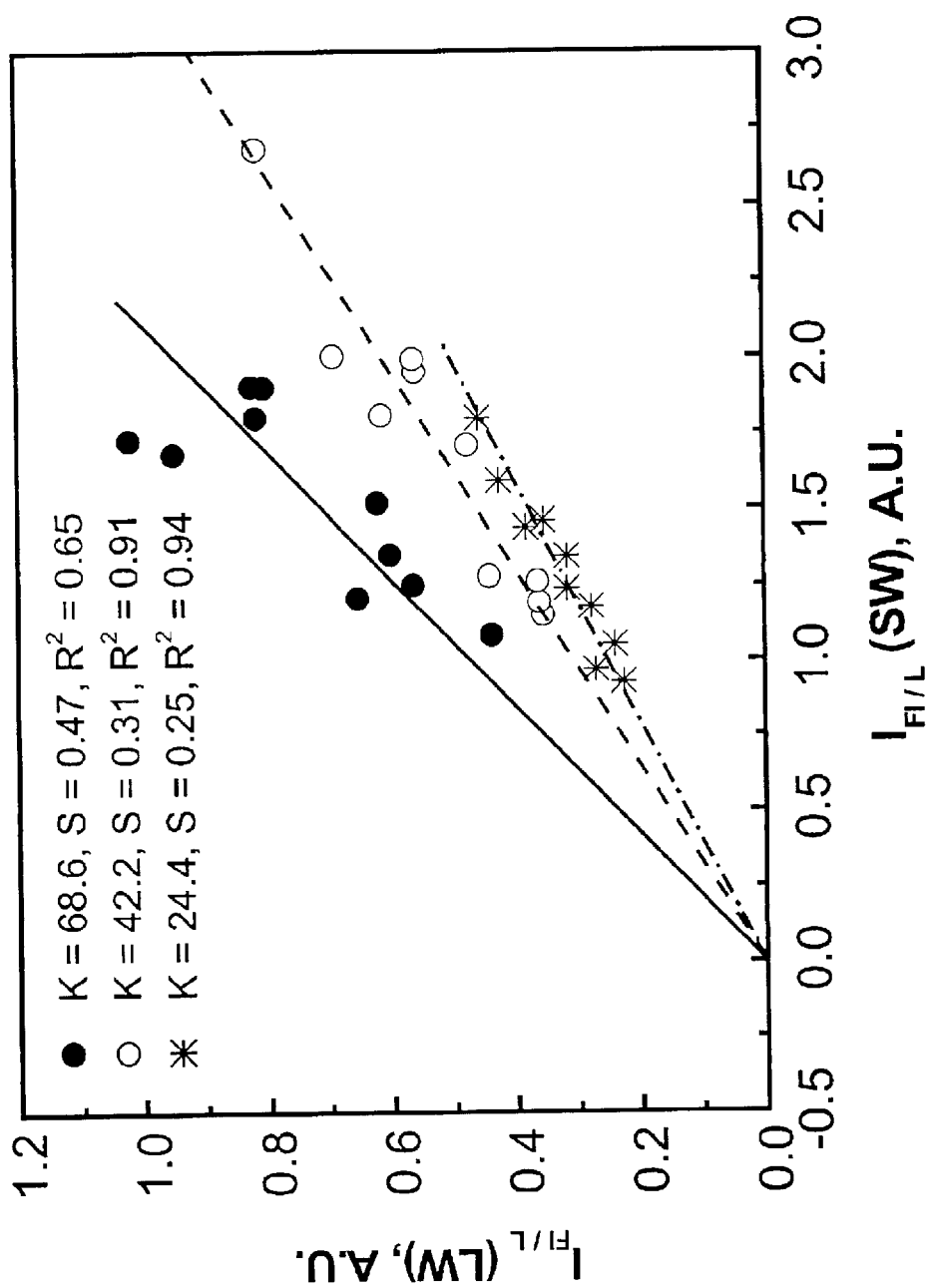
FIG. 16 shows a graph plotting fluorescence intensity per unit length from a long wavelength barrier/long-pass filter versus that from a short wavelength barrier/long-pass filter for fibres from pulp samples with three different Kappa numbers.
Figure 17:
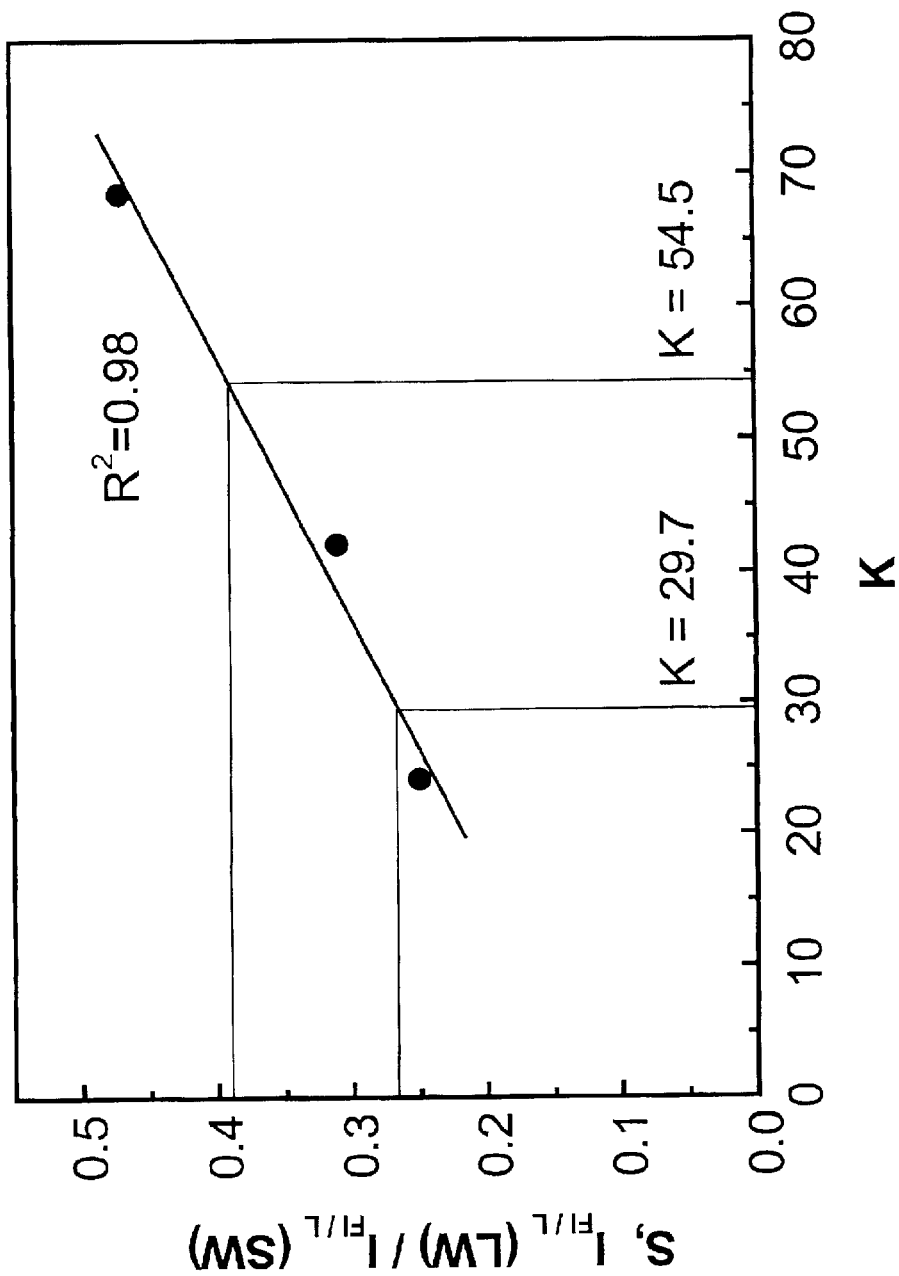
FIG. 17 shows a correlation between the fluorescence intensity ratios and the Kappa numbers for chemical pulps with different lignin contents.

FIG. 16 shows the fluorescence intensities per unit length $I_{FI/L}$ generated by using the long (LW) versus short (SW) wavelength barrier/long-pass/band-pass filters for individual wood pulp fibres from three pulps of different Kappa number. These data were generated with 365 nm excitation from a mercury arc lamp, and two long-pass filters with 420 nm for short and 520 nm for long cut-on wavelengths. The slopes of the fitted lines, which are shown to be different, correspond to the mean ratios of intensities between long and short wavelength filters for the three pulps. The values of the slopes are plotted against the measured Kappa numbers of these pulps by standard methods [10] as shown in FIG. 17. The coefficient of determination $R^2$ of 0.98 shows a strong correlation between this ratio and the Kappa number of wood pulp fibres. Therefore, this ratio can be used for the Kappa number of individual fibres. The present invention, therefore, will provide a process for determining the uniformity of Kappa number in a pulp. As also shown in FIG. 16, the different $R^2$ values for the fitted lines indicate the heterogeneity of Kappa number in the pulps. Pulps with higher Kappa number are shown to be more heterogeneous. Furthermore, this new invention can determine lignin content variability not only between but also within individual fibres.

Figure 18:
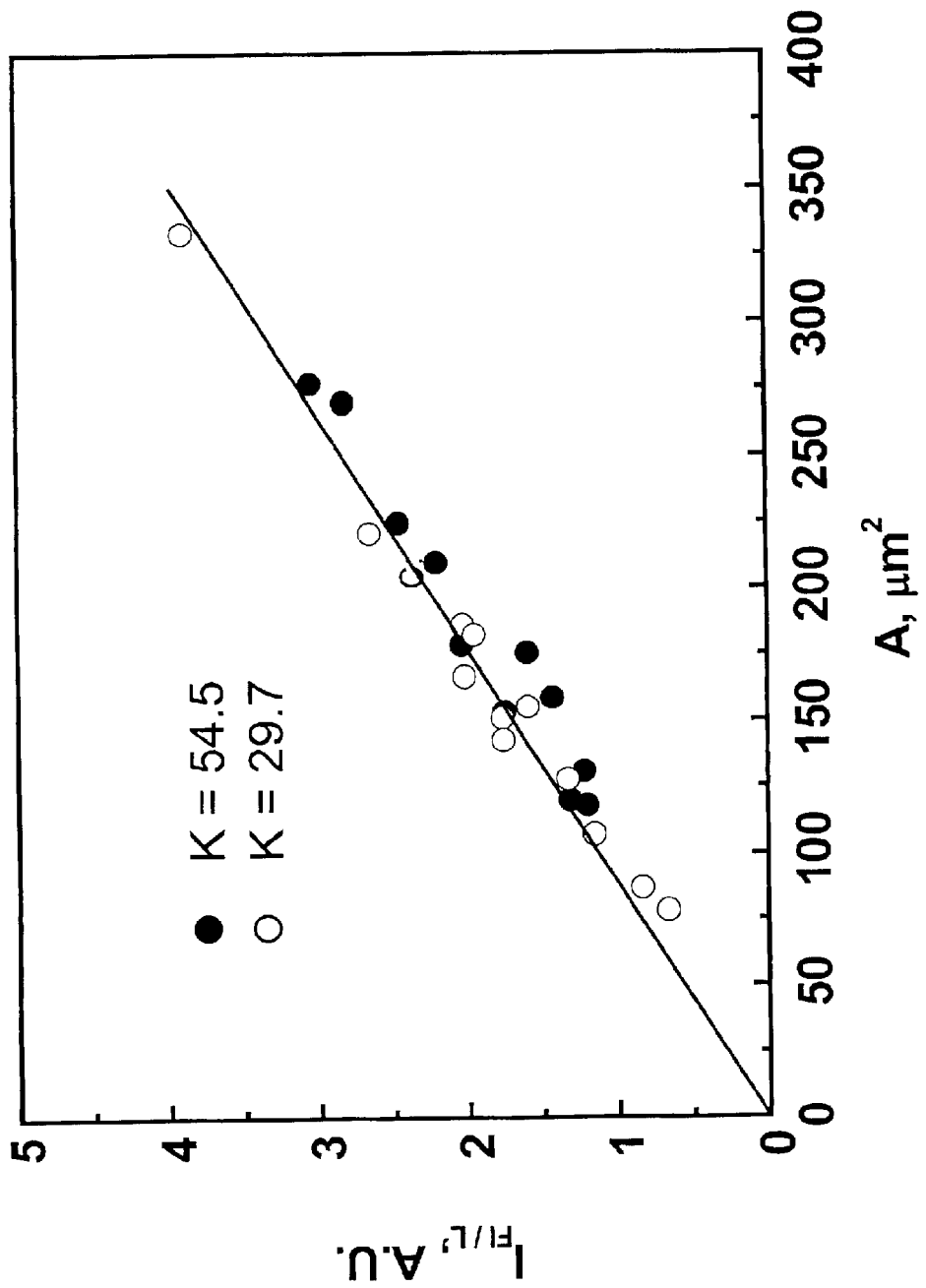
FIG. 18 shows a single calibration factor can be used for measuring fibre coarseness/cross-sectional area of wood pulp fibres with different Kappa numbers.

The information on Kappa number of individual fibres can be used to adjust the calibration factor between the fibre coarseness and its fluorescence intensity. For example, the higher Kappa number K corresponds to higher fluorescence intensity per unit length and higher intensity ratio as shown in FIGS. 15 and 17. If the intensity ratios for pulp with Kappa numbers 54.5 and 29.7 are used to adjust the calibration factor for fibres with different Kappa number as shown in FIG. 15, the fluorescence intensity per unit length will uniquely describe the fibre coarseness regardless of their Kappa number as shown in FIG. 18. This shows that both fibre coarseness and Kappa number K of an individual wood pulp fibre of unbleached chemical pulp fibres can be determined simultaneously from their fluorescence intensities I.

DESCRIPTION OF THE PREFERRED EMBODIMENTS

Figure 19:
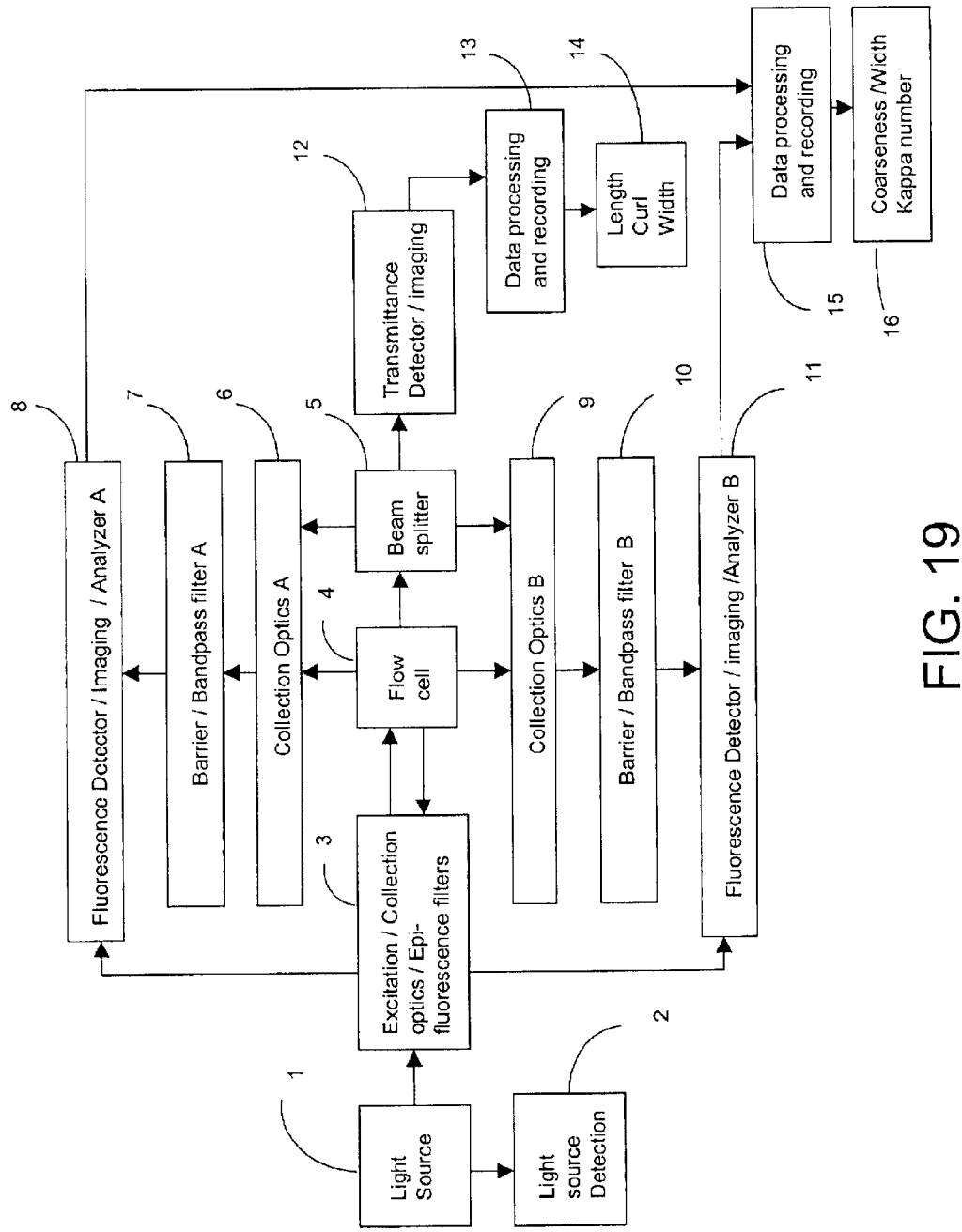
FIG. 19 shows a schematic block diagram of a system using fluorescence technique for measuring fibre physical and chemical properties according to the present invention.

FIG. 19 is a schematic block diagram of the major components of the present invention. Here are brief descriptions for each component.

Light source (1): The system comprises light source means for applying excitation light at a selected wavelength to fibres to produce fluorescence emission light having a spectral distribution of fluorescence intensity. The wavelength of the excitation light ranges from ultraviolet to visible light. The present invention can be applied for excitation by any source that provides measurable fluorescence intensity, for example, mercury arc lamp, a gas, dye, solid-state laser, laser diode, or Xenon lamp, and can be pulsed or continuous, or by direct illumination or illumination remotely through an optical fibre.

Light source detection (2): The system comprises a detector for monitoring the intensity of excitation light.

Excitation/collection optics and filters (3): The system comprises filters for selecting a single and/or multiple wavelengths for proper excitation, providing accurate measurements on coarseness and Kappa number of wood pulp fibres. The excitation/collection optics comprises lenses and/or fibre optics that deliver excitation light with desirable configuration to fibre sample, and that gathers the backward fluorescence emission light to detectors if needed. The excitation optics includes a laser scanning setup if necessary. The combined excitation/collection filter system, which includes excitation filter, dichroic mirror, and barrier filter, is a setup for epi-fluorescence. Epi-fluorescence technique is an option for collecting the backward emission light Flow cell (4): The system comprises a flow cell for fibres flowing through for rapid measurements such as in an online instrument. The cross-section of a flow cell can be square, rectangular, and circular in shape. The diameter of flow cell ranges from capillary size to few millimeters. The present invention works for fibres either moving or stationary.

Beam splitter (5): The system comprises a beam splitter so that excitation light will be continued for transmission imaging of fibres, and the forward fluorescence of fibres will also be collected and detected.

Collection optics (6, 9): The system comprises collection optics, lenses and/or fibre optics, that gather fluorescence emission light to detectors, and/or spectrometers, and/or that forms fluorescence images on cameras. The collection optics are used to collect the fluorescence signal in any direction, backward, forward, right and left. Collection optics A and B are used to collect fluorescence signals of different directions.

Barrier/bandpass filters (7, 10): The system comprises barrier/long-pass/band-pass filters A and B for selecting different and/or same regions of fluorescence emissions to be detected, analyzed, and/or imaged. The optical filters are chosen for providing accurate measurements on the coarseness and Kappa number of wood pulp fibres.

Fluorescence detector/imaging/spectral analyzer (8, 11): The system comprises light detectors for detecting the fluorescence intensity of the emission light, and/or for fluorescence imaging, and/or for determining the spectral distribution of fluorescence intensity and establishing signals indicative thereof. Any detector provides signal proportional to the fluorescence intensity whether it be a single and/or linear array detectors made of photomultiplier tubes, and/or solid-state devices, and/or a digital camera, and whether it be a one- or two-dimensional charge-couple device (CCD) and/or complementary metal-oxide semiconductor (CMOS) array camera for fluorescence intensity, and/or imaging and/or spectra analysis. These detectors provide measurements for fibre coarseness, width, and Kappa number of fibres (16). The detector systems A and B are used to detect fluorescence signals after the barrier/long-pass/band-pass filters A and B respectively.

Transmission detector/imaging (12): The system comprises light detectors, and/or a digital camera, and/or one- and/or two-dimensional CCD and/or CMOS cameras for detecting transmission intensity and/or image. Transmission image provides measurements for fibre length, curl, and width of fibres (14).

Data processing and recording (15): The system comprises means for recording, analyzing, and output the data.

With further reference to FIGS. 20, 21, 22 and 23, it has been determined in accordance with the invention that the fluorescence intensity is proportional to the mass of fibre-like particle being excited. As indicated above the fluorescence intensity $I_{FI}$ is proportional to the sample thickness.

Figure 20:
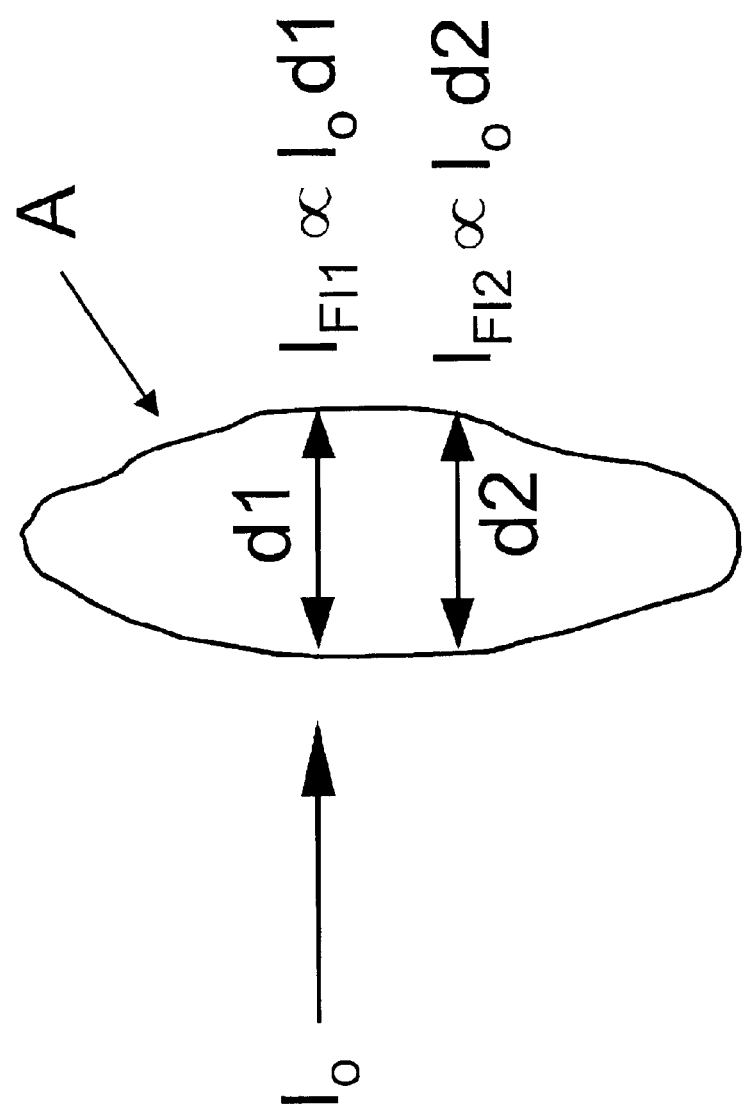
FIG. 20 is a diagram illustrating application of a small excitation beam, $I_o$, to a sample.

With reference to FIG. 20, the excitation beam, $I_o$, in this case refers to an infinitesimal small beam. As the excitation beam scans down the sample A, the fluorescence intensity is proportional to the thickness of the sample A that the beam transmitted through. This concept has been confirmed experimentally for wood pulp fibres as shown in FIGS. 3(*a*) and (*b*). This also shows that the fluorescence intensity is proportional to the mass of sample A (fibre-like particle) being excited. For example, the volume of the sample A being excited is d×δA, where d is the sample thickness, and δA is the cross-sectional area of the excitation beam $I_o$. The sample mass is related to the volume by the density of the material. Therefore, the mass of the sample A is obtained by collecting the fluorescence intensity from the sample as it is scanned by the excitation beam, such as a laser.

Figure 21:
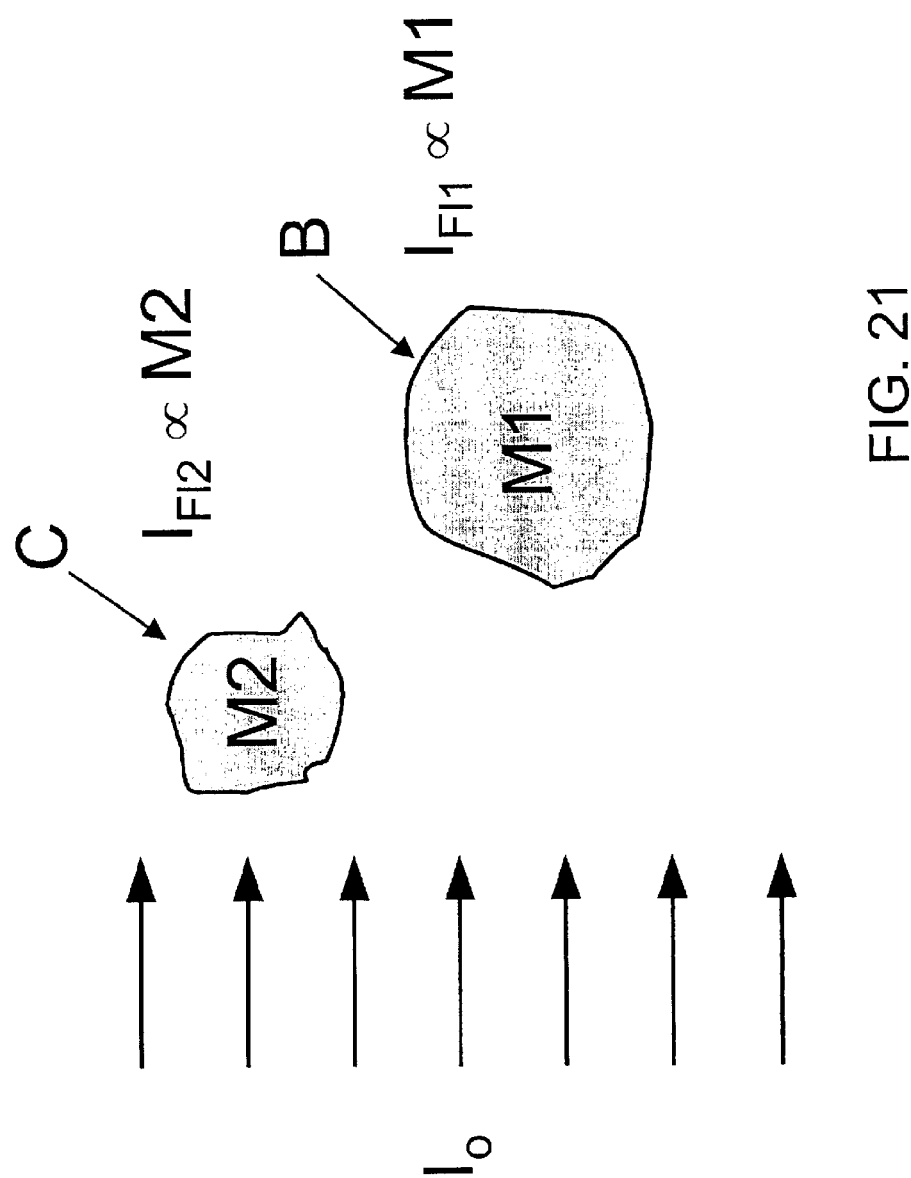
FIG. 21 is a diagram illustrating application of a large excitation beam, $I_o$, to samples of different mass.

In FIG. 21, the excitation beam $I_o$ is large compared to the size of samples B and C, and the fluorescence intensity is proportional to the mass of homogenous samples B and C. Thus the fluorescence intensity from samples B and C is proportional to their masses M1 and M2, respectively. This is accomplished by creating an even intensity excitation beam with a condenser.

Figure 22:
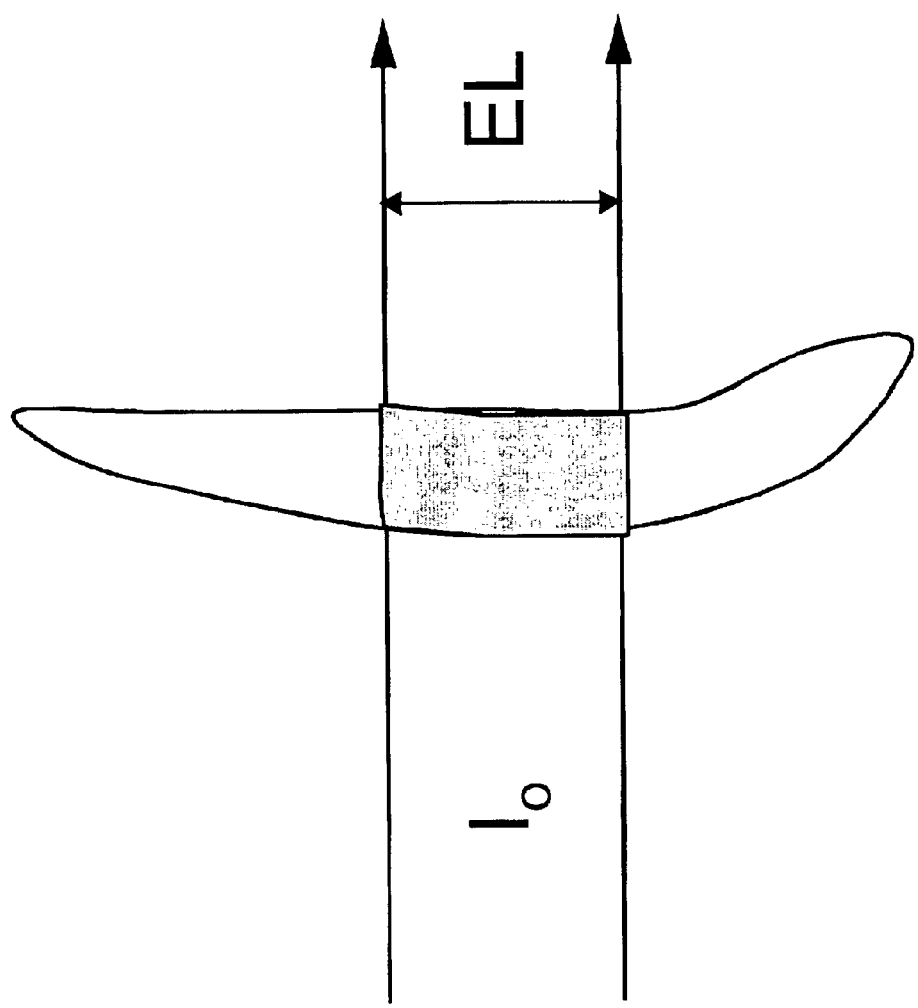
FIG. 22 is a diagram illustrating application of an excitation beam, $I_o$, to only a portion of a fibre sample.

In the case of a fibre-like sample, as illustrated in FIG. 22, if only a portion of the fibre is being excited, the fluorescence intensity will be proportional to the mass of that fibre portion. The fibre coarseness is proportional to the fluorescence intensity divided by the excitation length EL. This configuration is realized by creating a sheet of parallel excitation beam with the beam thickness being the excitation length EL as shown in FIG. 22. In general, the beam thickness can be ranged from a few micrometers to several millimeters.

Figure 23:
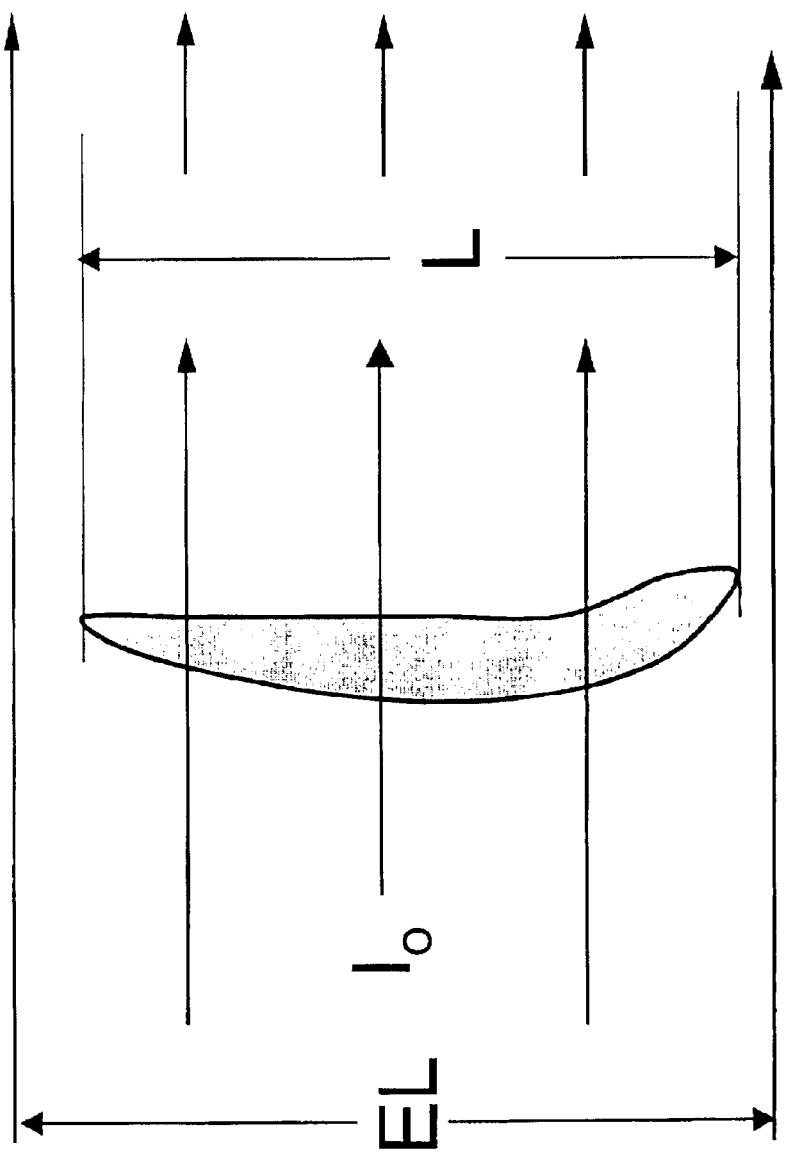
FIG. 23 is a diagram illustrating application of an excitation beam, $I_o$, to the whole of a fibre sample.

If the excitation length EL is long, and a whole fibre is being excited, as illustrated in FIG. 23, the fluorescence intensity is proportional to the mass of the whole fibre. The mean fibre coarseness of this fibre is proportional to the fluorescence intensity divided by the whole fibre length L.

References Referred to Herein

| | U.S. Pat. DOCUMENTS | | | |
|---|---|---|---|---|
| P1 | 5,311,290 | 5/1994 | Olson et al. | 356/383 |
| P2 | 5,293,219 | 3/1994 | Ayer | 356/383 |
| P3 | 5,486,915 | 1/1996 | Jeffers et al. | 356/318 |
| P4 | 4,837,446 | 6/1989 | Renard et al | 250/461.1 |
| | FOREIGN PATENT DOCUMENTS | | | |
| P5 | WO 99/15877 | 4/1999 | PCT Int'l Appl. | |

Other Publications

1 Seth, R. S., "Fibre quality factors in papermaking -II. The importance of fibre coarseness", in MRS Symposium Proceedings, Materials Research Society, Pittsburgh, Pa., Vol. 197, pp. 143–161 (1990).

2 Paavilainen, L. "Importance of cross-dimensional fibre properties and coarseness for the characterization of softwood sulphate pulp", Paperi ja Puu 75(5): 343 (1993).

3 Jang, H. F., Robertson, A. G., and Seth, R. S., "Transverse dimensions of wood pulp fibres by confocal laser scanning microscopy and image analysis", J. Mater. Sci. 27: pp. 6391–6400 (1992).

4 Seth, R. S., Jang, H. F., Chan, B. K., and Wu, C. B., "Transverse dimensions of wood pulp fibres and their implication for end use", in The Fundamentals of Papermaking Materials: Transactions of the Eleventh Fundamental Research Symposium held at Cambridge: September 1997, edited by C. F. Baker, PIRA International, Leatherhead, UK, pp. 473–503 (1997).

5 Boyer, B., and Rudie, A,. "Measurement of delignification diversity within kraft pulping processes", in TAPPI Proceedings, Pulp Conference, pp. 765–770 (1995).

6 Liu, Y., Gustafson, R., Callis, J., and McKean, W., "Fluorescence microphotometry in determining the lignin content of single pulp fibres", Preprints, $9^{th}$ International Symposium on Wood and Pulping Chemistry, Montreal, pp. T2-1–T2-5 (1997). Liu, Y., Gustafson, R., Callis, J., and McKean, W., "A novel method to measure fibre kappa number", TAPPI J. 82 (9), pp. 107–111 (1999). Liu, Y., Gustafson, R., Callis, J., and McKean, W., "Microspectroscopic analysis and kappa determination of single pulp fibres stained with acridine orange", J. Pulp Paper Sci. 25(10), pp. 351–355 (1999).

7 Olmstead, J. A. and Gray, D. G., "Fluorescence spectroscopy of cellulose, lignin and mechanical pulps: a review", J. Pulp and Paper Science 23(12), pp. 571–581 (1997).

8 Carlsson, J., Malmqvist, L., Nilsson, C. M. and Persson, W., "Application of optical fluorescence spectroscopy to paper production", Preprints, TAPPI Int. Paper Physics Conference, San Diego, pp. 429–436 (1999).

9 Sprent, P., "Applied Nonparametric Statistical Methods", Second edition, Chapman & Hall, New York, 1993.

G18—Kappa Number of Pulp", Standard Methods of the Technical Section of the CPPA, Montreal; "T236—Kappa Number of Pulp", TAPPI Standard Methods, TAPPI PRESS, Altanta.

| Nomenclature | |
|---|---|
| CLSM | Confocal laser scanning microscopy |
| CCD | Charge-couple device |
| CMOS | Complementary metal-oxide semiconductor |
| EL | Excitation length |
| d | Sample thickness |
| FM | Fluorescence microscoy technique |
| LW | Long wavelength |
| $I_o$ | Intensity of excitation light |
| $I_{FL}$ | Fluorescence intensity |
| $I_{FL/L}$ | Fluorescence intensity per unit length |
| M | Sample mass |
| SW | Short wavelength |
| Mathematics terminology | |
| A.U. | Arbitrary unit |
| CDF | Cumulative distribution function |
| K-S | Kolmogorov-Simirnor test |
| n | Number of measurements |
| $R^2$ | Coefficient of determination |
| S | Slope of linear fit line |
| Fibre | |
| A | Fibre wall cross-sectional area |
| L | Fibre length |
| K | Kappa number |
| OFP | Outer fibre perimeter |
| P | Centre-line perimeter |
| T | Fibre wall thickness |
| W | Fibre width |
| VT | Vertical fibre wall thickness |
| TMP | Thermomechanical pulp |
| Wood species | |
| AS | Aspen |
| BS | Black spruce |
| EU | Eucalyptus |
| SP | Southern pine |
| WH | Western hemlock |
| WS | Western spruce |

What is claimed is:

1. A method of determining a physical property of wood pulp comprising:
   a) applying excitation light at at least one predetermined wavelength to wood pulp, to produce fluorescence emission light from individual fibre particles of said pulp,
   b) detecting fluorescence intensity of said fluorescence emission light, for each said predetermined wavelength, and
   c) determining a physical property of individual fibre particles of the wood pulp from said fluorescence intensities.

2. A method according to claim 1 wherein at least a single wavelength of excitation light in the range 5 nm to 700 nm is applied in step a).

3. A method according to claim 2 wherein said excitation light has a wavelength of 250 nm to 600 nm.

4. A method according to claim 3 wherein said wavelength is 360 nm to 500 nm.

5. A method according to claim 1 wherein step c) comprises determining fibre thickness in said wood pulp from the detected fluorescence intensity in b).

6. A method according to claim 1 wherein step c) comprises determining fibre cross-sectional area in said wood pulp from area under a fluorescence intensity profile derived from the detected fluorescence intensity in b).

7. A method according to claim 1 wherein said step c) comprises determining fibre coarseness in said wood pulp from the detected fluorescence intensity per unit length in step b).

8. An apparatus for determining a physical property of wood pulp comprising:
   i) means to apply excitation light at at least one predetermined wavelength to wood pulp, to produce fluorescence emission light from individual fibre particles of the wood pulp,
   ii) detection means for detecting fluorescence intensity of the fluorescence emission light for each predetermined wavelength, and
   iii) means for determining a physical property of individual fibre particles of the wood pulp from the fluorescence intensities.

9. An apparatus according to claim 8 wherein said means i) applies excitation light at at least a single wavelength in the range 5 nm to 700 nm, and means iii) determines a physical property of individual fibre particles of the wood pulp.

10. An apparatus according to claim 9 wherein said wavelength is 250 nm to 600 nm.

11. An apparatus according to claim 9 wherein said wavelength is 360 nm to 500 nm.

* * * * *